US009517070B2

(12) United States Patent
Mulreed

(10) Patent No.: US 9,517,070 B2
(45) Date of Patent: Dec. 13, 2016

(54) ANVIL ASSEMBLY AND DELIVERY SYSTEM

(71) Applicant: Covidien LP, Mansfield, MA (US)

(72) Inventor: Jeffrey Mulreed, Shelton, CT (US)

(73) Assignee: Covidien LP, Mansfield, MA (US)

( * ) Notice: Subject to any disclaimer, the term of this patent is extended or adjusted under 35 U.S.C. 154(b) by 480 days.

(21) Appl. No.: 14/078,814

(22) Filed: Nov. 13, 2013

(65) Prior Publication Data
US 2015/0129636 A1 May 14, 2015

(51) Int. Cl.
*A61B 17/115* (2006.01)
*A61B 17/068* (2006.01)
*A61B 17/11* (2006.01)
A61B 17/072 (2006.01)
A61B 17/06 (2006.01)

(52) U.S. Cl.
CPC ........ *A61B 17/1155* (2013.01); *A61B 17/1114* (2013.01); *A61B 17/06123* (2013.01); *A61B 2017/07257* (2013.01)

(58) Field of Classification Search
CPC ............ A61B 17/12154; A61B 17/068; A61B 2017/1142; A61B 2017/1157; A61B 2017/1132; A61B 17/1114; A61B 2017/07257; A61B 17/06123
USPC .................... 227/175.1, 176.1, 178.1, 179.1, 180.1,227/181.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |

(Continued)

FOREIGN PATENT DOCUMENTS

| | | |
|---|---|---|
| CA | 908529 | 8/1972 |
| DE | 1057729 B | 5/1959 |

(Continued)

OTHER PUBLICATIONS

European Search Report EP 14192785 dated Feb. 26, 2015.

*Primary Examiner* — Robert Long
*Assistant Examiner* — Xavier A Madison

(57) ABSTRACT

An anvil assembly suitable for trans-oral delivery includes an anvil head configured to receive a guide suture that is severed during a stapling procedure. An anvil delivery assembly includes the anvil assembly and a suture guide assembly secured to the anvil assembly.

15 Claims, 21 Drawing Sheets

(56) References Cited

U.S. PATENT DOCUMENTS

| | | |
|---|---|---|
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |

(56) References Cited

U.S. PATENT DOCUMENTS

| | | |
|---|---|---|
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |

(56) References Cited

U.S. PATENT DOCUMENTS

| | | |
|---|---|---|
| 8,066,169 B2 | 11/2011 | Viola |
| 8,070,035 B2 | 12/2011 | Holsten et al. |
| 8,070,037 B2 | 12/2011 | Csiky et al. |
| 8,109,426 B2 | 2/2012 | Milliman et al. |
| 8,272,552 B2 | 9/2012 | Holsten et al. |
| 8,317,073 B2 | 11/2012 | Milliman et al. |
| 8,328,063 B2 | 12/2012 | Milliman et al. |
| 8,343,185 B2 | 1/2013 | Milliman et al. |
| 8,360,295 B2 | 1/2013 | Milliman et al. |
| 8,403,942 B2 | 3/2013 | Milliman et al. |
| 8,418,905 B2 | 4/2013 | Milliman |
| 8,424,535 B2 | 4/2013 | Hessler et al. |
| 8,453,910 B2 | 6/2013 | Bettuchi |
| 8,453,911 B2 | 6/2013 | Milliman et al. |
| 8,485,414 B2 | 7/2013 | Criscuolo |
| 8,490,853 B2 | 7/2013 | Criscuolo |
| 8,590,763 B2 | 11/2013 | Milliman |
| 8,608,047 B2 | 12/2013 | Holsten et al. |
| 8,616,428 B2 | 12/2013 | Milliman et al. |
| 8,616,429 B2 | 12/2013 | Viola |
| 8,631,993 B2 | 1/2014 | Kostrzewski |
| 2003/0111507 A1 | 6/2003 | Nunez |
| 2004/0087977 A1 | 5/2004 | Nolan et al. |
| 2005/0051597 A1 | 3/2005 | Toledano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0272722 A1 | 11/2007 | Aranyi |
| 2009/0082785 A1 | 3/2009 | Milliman et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2012/0104073 A1 | 5/2012 | Milliman et al. |
| 2012/0125972 A1 | 5/2012 | Holsten et al. |
| 2012/0145766 A1 | 6/2012 | Milliman et al. |
| 2012/0153005 A1 | 6/2012 | Milliman |
| 2012/0168487 A1 | 7/2012 | Holsten et al. |
| 2012/0193395 A1 | 8/2012 | Pastorelli et al. |
| 2012/0193398 A1 | 8/2012 | Williams et al. |
| 2012/0228356 A1 | 9/2012 | Milliman et al. |
| 2012/0228357 A1 | 9/2012 | Milliman |
| 2012/0232339 A1 | 9/2012 | Csiky |
| 2012/0248173 A1 | 10/2012 | Milliman et al. |
| 2012/0273548 A1 | 11/2012 | Ma et al. |
| 2012/0280018 A1 | 11/2012 | Hessler |
| 2012/0292368 A1 | 11/2012 | Nalagatla et al. |
| 2012/0298721 A1 | 11/2012 | Bettuchi |
| 2012/0305625 A1 | 12/2012 | Milliman et al. |
| 2012/0305629 A1 | 12/2012 | Orban et al. |
| 2012/0325888 A1 | 12/2012 | Qiao et al. |
| 2012/0325892 A1 | 12/2012 | Kostrzewski |
| 2013/0015232 A1 | 1/2013 | Smith |
| 2013/0020372 A1 | 1/2013 | Jankowski |
| 2013/0020373 A1 | 1/2013 | Smith et al. |
| 2013/0032628 A1 | 2/2013 | Li |
| 2013/0037599 A1 | 2/2013 | Rebuffat et al. |
| 2013/0056516 A1 | 3/2013 | Viola |
| 2013/0056517 A1 | 3/2013 | Patel et al. |
| 2013/0060258 A1 | 3/2013 | Giacomantonio |
| 2013/0068817 A1 | 3/2013 | Milliman et al. |
| 2013/0068819 A1 | 3/2013 | Viola |
| 2013/0105546 A1 | 5/2013 | Milliman et al. |
| 2013/0105549 A1 | 5/2013 | Holsten et al. |
| 2013/0105551 A1 | 5/2013 | Zingman |
| 2013/0126580 A1 | 5/2013 | Smith et al. |
| 2013/0126587 A1 | 5/2013 | Bettuchi et al. |
| 2013/0153630 A1 | 6/2013 | Miller et al. |
| 2013/0153631 A1 | 6/2013 | Vasudevan et al. |
| 2013/0153633 A1 | 6/2013 | Casasanta et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181029 A1 | 7/2013 | Milliman |
| 2013/0181035 A1 | 7/2013 | Milliman |
| 2013/0181036 A1 | 7/2013 | Olson et al. |
| 2013/0186930 A1 | 7/2013 | Wenchell |
| 2013/0193185 A1 | 8/2013 | Patel |
| 2013/0193187 A1 | 8/2013 | Milliman |
| 2013/0193190 A1 | 8/2013 | Carter |

(56) References Cited

U.S. PATENT DOCUMENTS

| | | |
|---|---|---|
| 2013/0193191 A1 | 8/2013 | Stevenson et al. |
| 2013/0193192 A1 | 8/2013 | Casasanta et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams et al. |
| 2014/0012317 A1 | 1/2014 | Orban et al. |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2524656 A2 | 11/2012 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | WO 8706448 A | 11/1987 |
| WO | WO 8900406 A1 | 1/1989 |
| WO | WO 9006085 A | 6/1990 |
| WO | WO 01/54594 A1 | 8/2001 |
| WO | WO 2008/107918 A1 | 9/2008 |

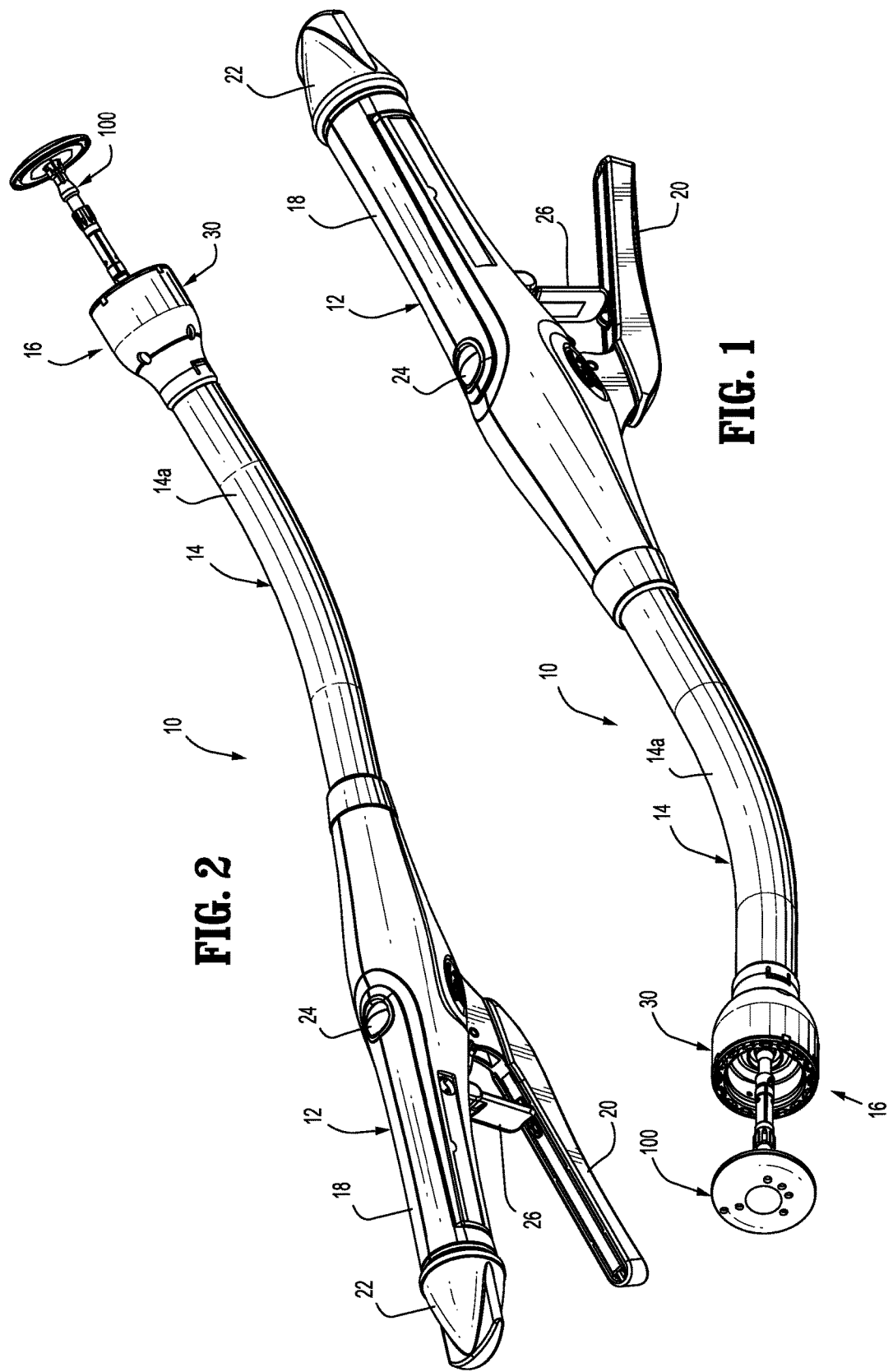

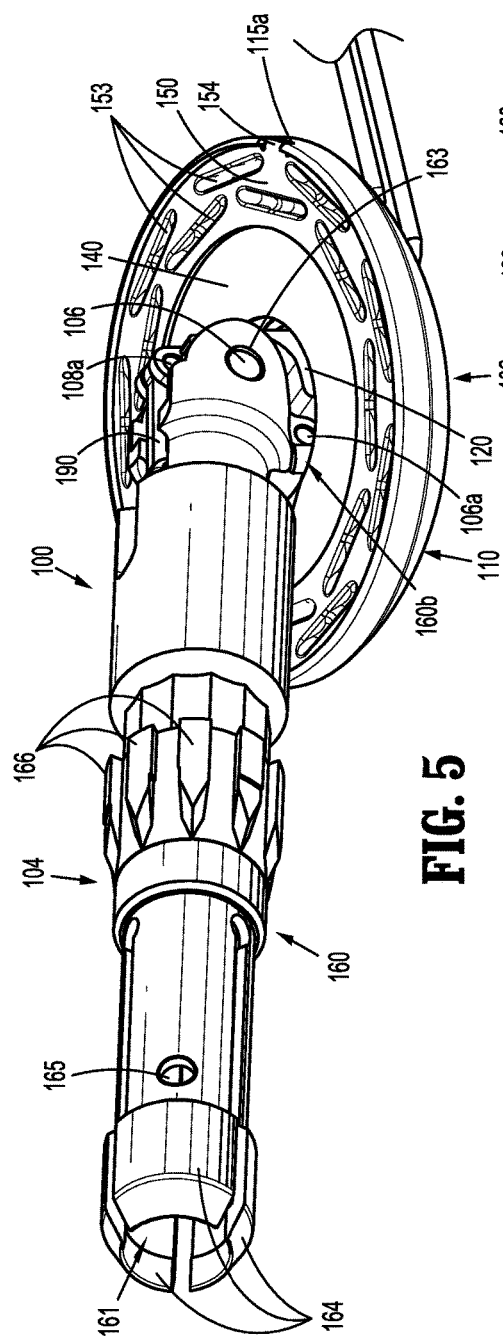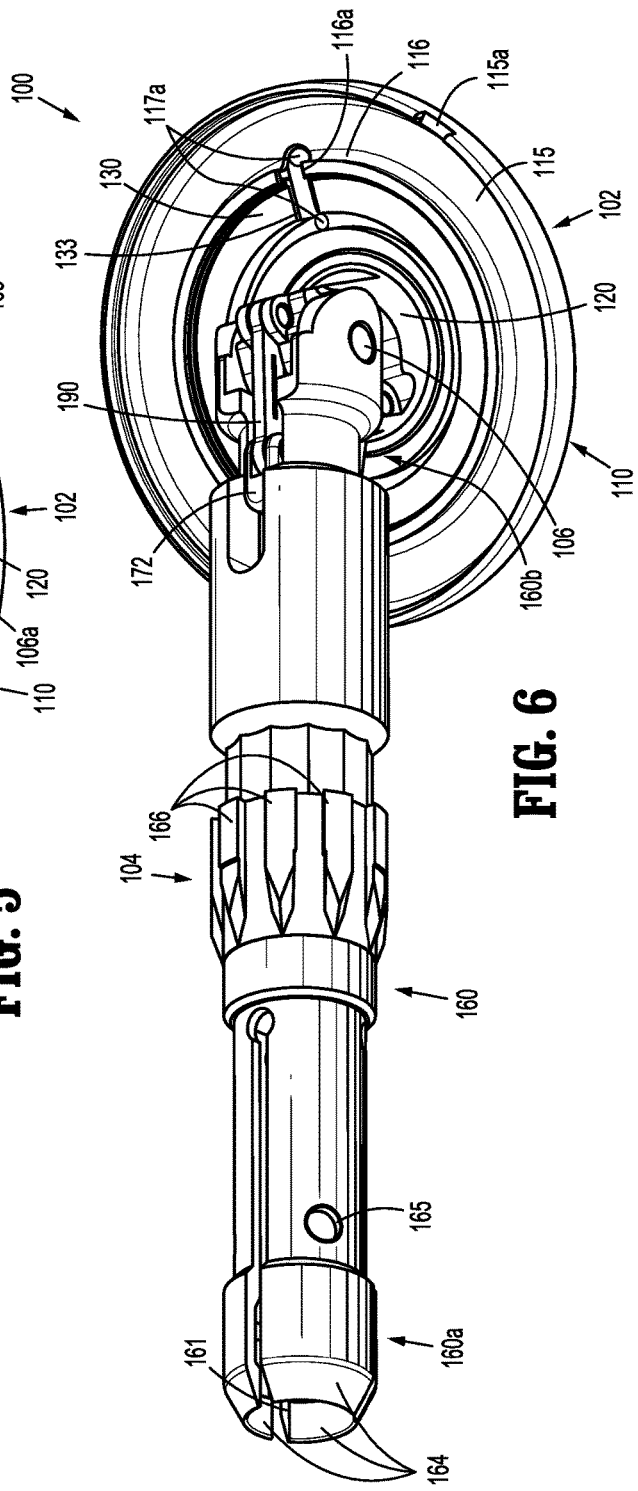

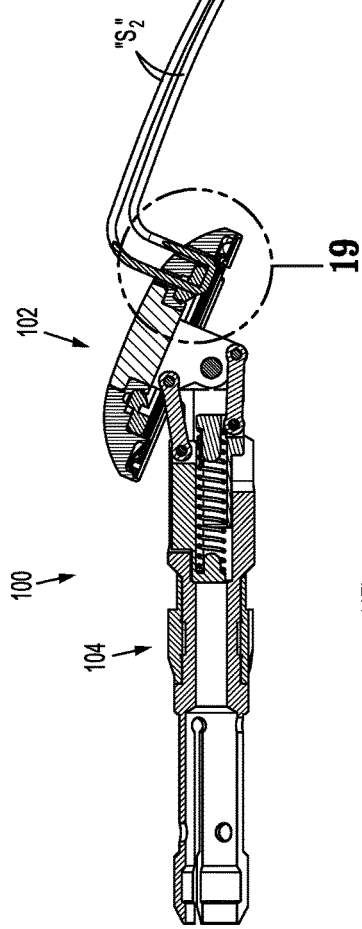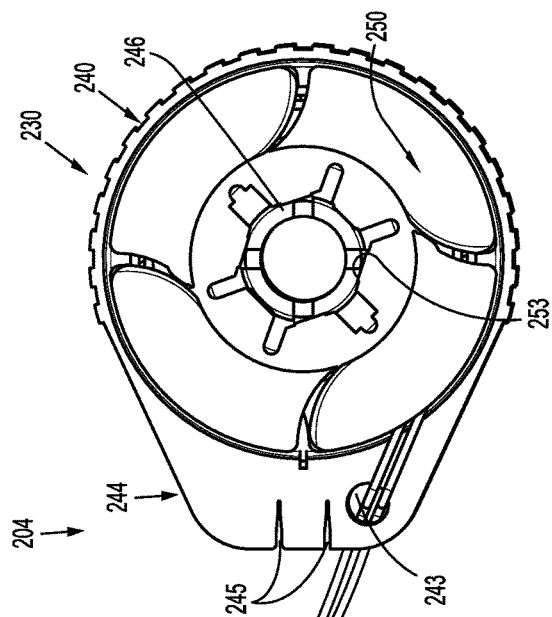
FIG. 18
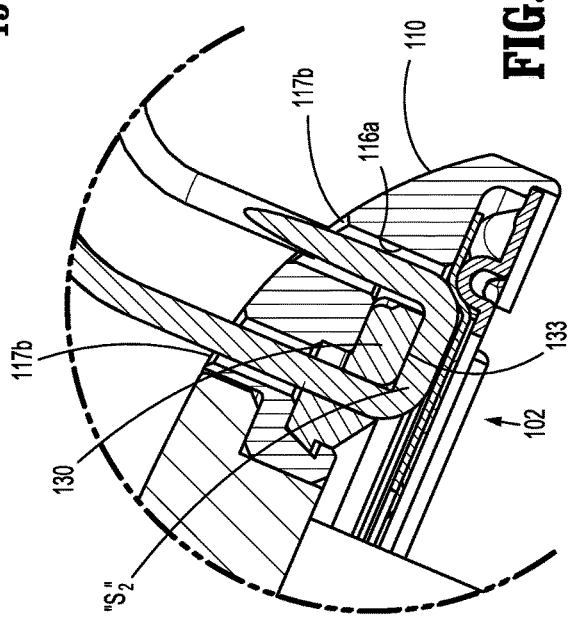
FIG. 19

ANVIL ASSEMBLY AND DELIVERY SYSTEM

BACKGROUND

Technical Field

The present disclosure relates to an anvil assembly for use with a surgical stapling device. More particularly, the present disclosure relates to an anvil assembly and a system for trans-oral delivery of the anvil assembly.

Background of Related Art

Anastomosis is the surgical joining of separate hollow organ sections to allow the sections to communicate with each other. Typically, an anastomosis procedure follows surgery in which a diseased or defective section of hollow tissue is removed and the remaining end sections are to be joined. Depending on the desired anastomosis procedure, the end sections of the hollow organ may be joined using circular, end-to-end, end-to-side, or side-to-side organ reconstruction methods.

In a circular anastomosis procedure, the two ends of the organ sections are joined by means of a surgical stapling instrument which drives a circular array of staples through the organ end sections and cores and removes any overlapping tissue to free a tubular passage. In some applications of a circular anastomosis procedure, an anvil rod having an attached anvil head is mounted to the distal end of a surgical stapling instrument shaft prior to insertion of the instrument into the tissue to be anastomosed. However, in other applications, a detachable anvil rod may be mounted to the instrument subsequent to positioning of the surgical stapling instrument and the anvil assembly within respective tissue sections. In such instances, the surgical stapling instrument and the anvil assembly are separately delivered to the operative site. Each tissue end section is then secured to a respective anvil or staple holding component, e.g., by a purse string suture. The anvil assembly is mounted to the surgical stapling instrument by inserting a mounting portion of the anvil rod within the distal end of the surgical stapling instrument so that a mounting mechanism within the surgical stapling instrument securely engages the anvil rod. Preparation of the tissue sections to be joined and mounting of the anvil rod to the surgical stapling instrument may be performed using minimally invasive surgical techniques, i.e., under laparoscopic guidance.

An anvil assembly delivery system for delivering an anvil assembly trans-orally to a surgical site, e.g., the stomach, is disclosed in commonly owned U.S. Pat. No. 8,109,426, the content of which is incorporated herein by reference in its entirety. As described, a guide suture is threaded through openings in the head of the anvil assembly to facilitate trans-oral insertion of the anvil assembly and to allow retrieval of the anvil assembly prior to attachment of the anvil assembly to the surgical stapling instrument. At any point during the stapling procedure, the guide suture may be detached from the anvil assembly by pulling the guide suture back through the openings in the anvil head.

To prevent premature detachment of the guide suture from the anvil assembly during trans-oral insertion, it would be beneficial to have an anvil assembly that is configured such that the guide suture remains attached to the anvil assembly until the stapling procedure is compete, i.e., after the tissue to be anastomosed has been stapled and cut.

SUMMARY

In accordance with the present disclosure, an anvil assembly is provided for use with a surgical stapling instrument for performing end-to-end anastomosis of tissue. The anvil assembly includes an anvil center rod, and a head assembly pivotally secured to the anvil center rod about a pivot axis and movable between an operative position and a tilted position. The head assembly includes an anvil head and a cutting ring disposed within the anvil head. The anvil head defines first and second openings and the cutting ring defining a slot in alignment with the first and second openings.

In one embodiment, the first and second openings and the slot are dimensioned to receive a suture. The anvil center rod may include first and second slide members. The first slide member may be pivotally connected to the head assembly on one side of the pivot axis by a first drive link and the second slide member being connected to the head assembly on the other side of the pivot axis by a second drive link. The first slide member may be movable in relation to the second slide member to effect movement of the head assembly between the operative position and the tilted position. The anvil assembly may further include a biasing member positioned to urge the first slide member in relation to the second slide member to position the head assembly in the tilted position. The biasing member may be positioned between the first member and the second slide member to urge the first and second slide members apart.

Also provided is an anvil delivery system including an anvil assembly and a suture guide assembly. The suture guide assembly includes a guide suture secured to the head assembly and a reel assembly configured for selectively dispensing the guide suture. The guide suture may be received through the first opening in the anvil head, passes through the slot in the cutting ring, and extends from the second opening in the anvil head. The reel assembly may include a housing and a reel member rotatably received within the housing. The guide suture may be supported about the reel member. The reel member may define an annular channel for receiving the guide suture. The housing may define an annular cavity. The reel member may be rotatably supported on the housing within the annular cavity.

In some embodiments, the anvil delivery system may further include a tubular guide assembly for trans-oral insertion of the anvil assembly. The tubular guide assembly may include a flexible tube and an adapter configured for operably connecting the flexible tube to the anvil center rod. The tubular guide assembly may further include a retaining suture for retaining the head assembly of the anvil assembly in the tilted position. The retaining suture may be received through third and fourth openings in the anvil head and may be secured between the adapter and the flexible tube.

Also provided is an anvil delivery kit. The kit including an anvil assembly, a suture guide assembly including a guide suture and a reel assembly, and a tubular guide assembly including a flexible tube and an adapter.

BRIEF DESCRIPTION OF THE DRAWINGS

Embodiments of the presently disclosed surgical stapling instrument, anvil assembly, and anvil delivery system are described hereinbelow with reference to the drawings wherein:

FIG. 1 is a top side perspective view from the proximal end of the presently disclosed surgical stapling device in the unapproximated position;

FIG. 2 is a top side perspective view from the distal end of the surgical stapling device shown in FIG. 1;

FIG. 5 is a perspective view from the proximal end of the anvil assembly of the surgical stapling device shown in FIGS. 1 and 2, with the anvil head in a tilted reduced profile position;

FIG. 6 is a perspective view of the anvil assembly shown in FIG. 5 with the anvil head in the tilted reduced profile position and the anvil plate and cover removed;

FIG. 18 is a cross-sectional view taken along section line 18-18 of FIG. 17;

FIG. 19 is an enlarged view of indicated area of detail shown in FIG. 18;

DETAILED DESCRIPTION OF THE DRAWINGS

Figure 3:
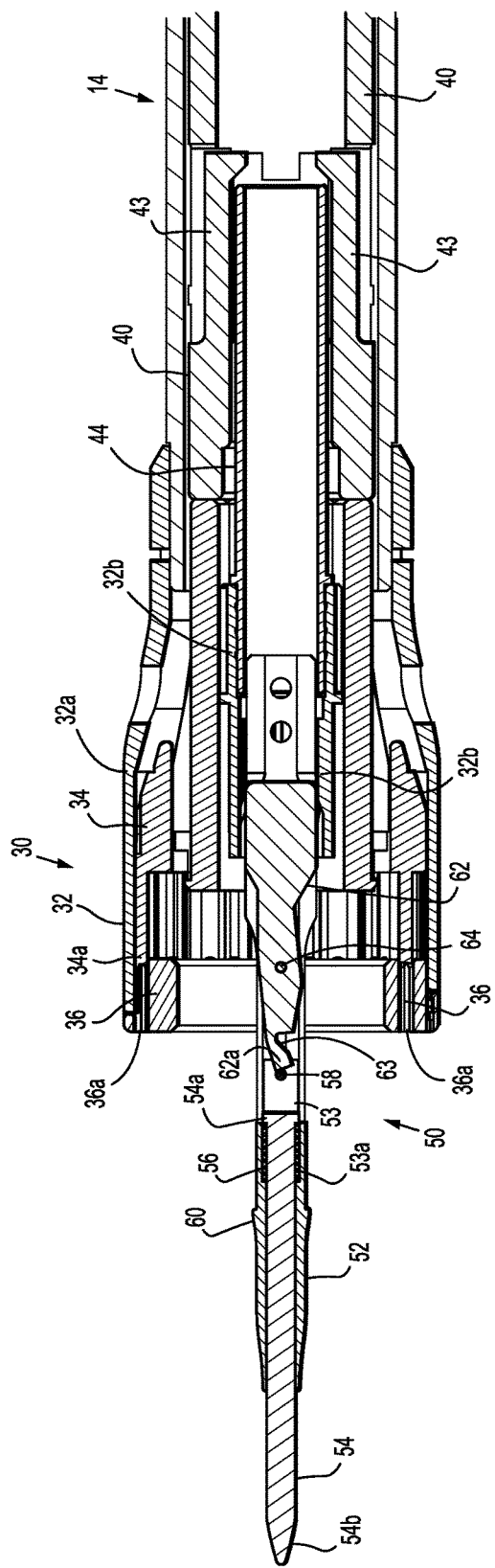
FIG. 3 is a side cross-sectional view of the distal end of the central body portion and distal head portion of the surgical stapling device shown in FIGS. 1 and 2, with the anvil assembly removed.

Embodiments of the presently disclosed surgical stapling device, anvil assembly, and anvil delivery system will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Referring to FIGS. 1 and 2, a surgical stapling instrument including an anvil assembly according to the present disclosure is shown generally as stapling device 10. Briefly, stapling device 10 includes a proximal handle assembly 12, an elongated central body portion 14 including a curved elongated outer tube 14a, and a distal head portion 16. Handle assembly 12 includes a stationary handle 18, a firing trigger 20, a rotatable approximation knob 22, and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 100 and a shell assembly 30. The structure and function of stapling device 10 will only be described to the extent necessary to fully disclose the operation of anvil assembly 100. For a more detailed description of an exemplary stapling device, please refer to commonly owned U.S. Pat. No. 7,364,060, ("the '060 patent") the content of which is incorporated herein by reference in its entirety.

Although a manual handle assembly is described, the surgical stapling device may be a powered (e.g., motor operated) surgical instrument, or part of a robotic surgical system, in any of the embodiments disclosed herein.

Figure 4:
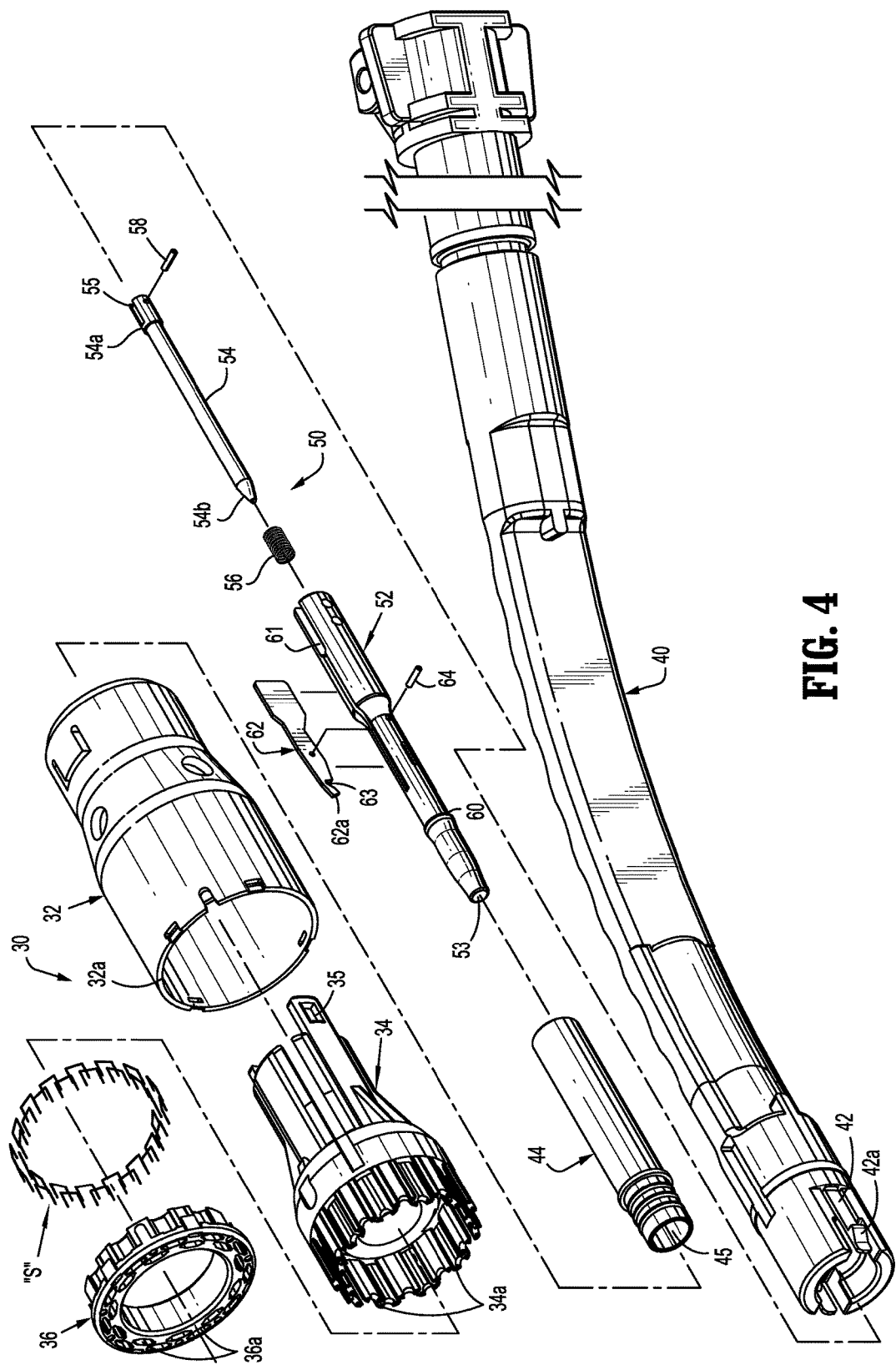
FIG. 4 is a side exploded perspective view of the distal head portion, anvil retainer assembly and pusher back of the surgical stapling device shown in FIGS. 1 and 2.

With reference now to FIGS. 3 and 4, distal end portion 16 of stapling device 10 includes shell assembly 30 which is secured to a distal end of the central body portion 14, a pusher 40 extending distally through central body portion 14, and an anvil retainer assembly 50 extending through pusher 40 and shell assembly 30. Although not shown, anvil retainer assembly 50 is operably connected to an approximation mechanism of stapling device 10 which is actuated by the rotatable approximation knob 22 (FIG. 1), and pusher 40 is operably connected to a firing mechanism of stapling device 10 which is actuated by the firing trigger 20 (FIG. 1). For a more detailed description of the approximation mechanism and/or the firing mechanism of the stapling device 10, see the '060 patent which has been incorporated herein by reference.

Shell assembly 30 includes a shell or housing 32, a pusher back 34, a staple guide 36, a cylindrical knife 38 (FIG. 25), and a plurality of staples "S". Shell 32 includes an outer housing portion 32a and an inner housing portion 32b (FIG. 3). Staple guide 36 is supported in the distal end of outer housing portion 32a and includes an annular array of staple receiving pockets 36a for housing staples "S". Pusher back 34 is slidably supported in shell 32 between outer housing portion 32a and inner housing portion 32b and includes a plurality of fingers 34a which are each slidably received in respective staple pockets 36a in staple guide 36. Pusher back 34 includes a pair of recesses 35 which receive detents 42a formed on flexible fingers 42 of a pusher 40 to secure pusher 40 to pusher back 34 such that pusher back 34 is movable with pusher 40 from a retracted position to an advanced position to eject staples "S" from staple guide 36.

In any of the embodiments disclosed herein, the shell assembly may be configured as a removable and replaceable assembly. In this way, after the staples are fired, the shell assembly can be replaced, providing a new set of staples, even staples of a different size or configuration, and a fresh knife.

An elongated hollow bushing 44 is fixedly retained in inner housing portion 32b of shell 32 using, e.g., screw threads, a friction fitting, or the like. Bushing 44 defines a channel 45 through which anvil retainer assembly 50 and anvil center rod 160 reciprocate during approximation and separation of anvil assembly 100 and shell assembly 30. Bushing 44 provides additional strength to inner housing portion 32b of shell 32 to prevent separation of the anvil assembly 100 and anvil retainer assembly 50 during firing of the stapling device 10.

Anvil retainer assembly 50 includes a two-part assembly having a body portion 52 defining a longitudinal throughbore 53 and a trocar or locking member 54 slidably received within longitudinal throughbore 53. Longitudinal throughbore 53 includes a stepped portion or shoulder 53a (FIG. 3).

Trocar 54 includes an annular flange or shoulder 54a on a proximal end and a blunt tip 54b on a distal end. Tip 54b of trocar 54 extends from the distal end of body portion 52 of anvil retainer assembly 50 and is movable within throughbore 53 of body portion 52 from an advanced position to a retracted position. A biasing member, e.g., a coil spring 56, is positioned between annular flange 54a and shoulder 53a of longitudinal bore 53 (FIG. 3). The biasing member 56 urges trocar 54 to its retracted position. The proximal end of trocar 54 includes a transverse slot 55 having a pin or rod 58 extending therethrough. Pin 58 is slidably positioned within longitudinal slots 55 formed in body portion 52. The distal and proximal ends of slots 51 define the advanced and retracted positions of trocar 54, respectively.

Body portion 52 of anvil retainer assembly 50 includes an annular protrusion 60 and defines a longitudinal slot 61. Annular protrusion 60 facilitates attachment of anvil assembly 100 to anvil retainer assembly 50 as will be discussed in further detail below. A cam member 62 is pivotally supported about a pivot member 64 in slot 61 at a position proximal of pin 58. Cam member 62 includes a distal finger 62a having an angled face and a recess 63 positioned proximally of finger 62a for receiving pin 58 of trocar 54. Pin 58 is urged by coil spring 56 towards finger 62a. Engagement between the angled face of finger 62a and pin 58 urges cam member 62 to pivot about pivot member 64 to allow pin 58 to move into recess 63.

Figure 7:
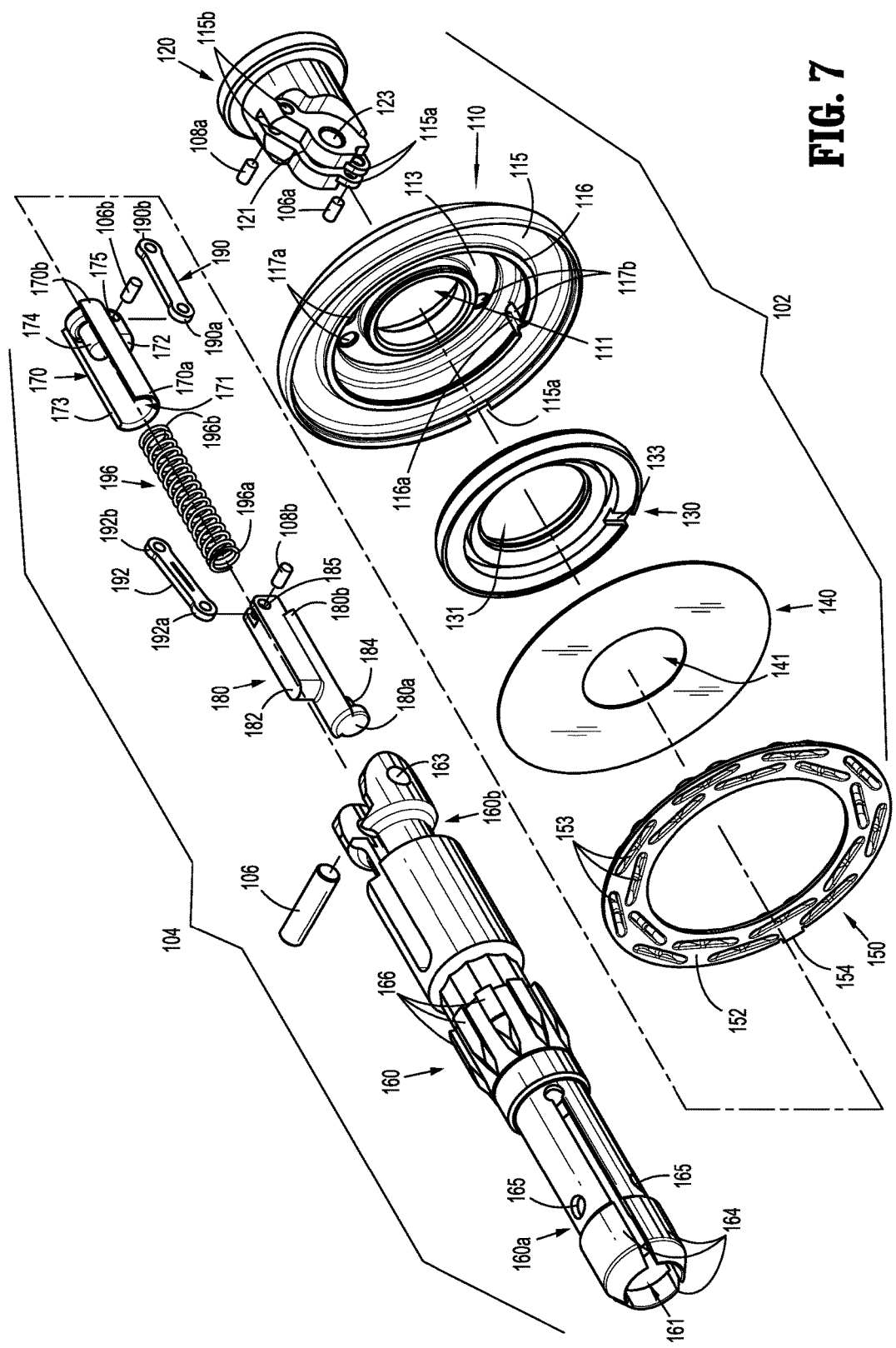
FIG. 7 is an exploded side perspective view of the anvil assembly shown in FIG. 5.
Figure 21:
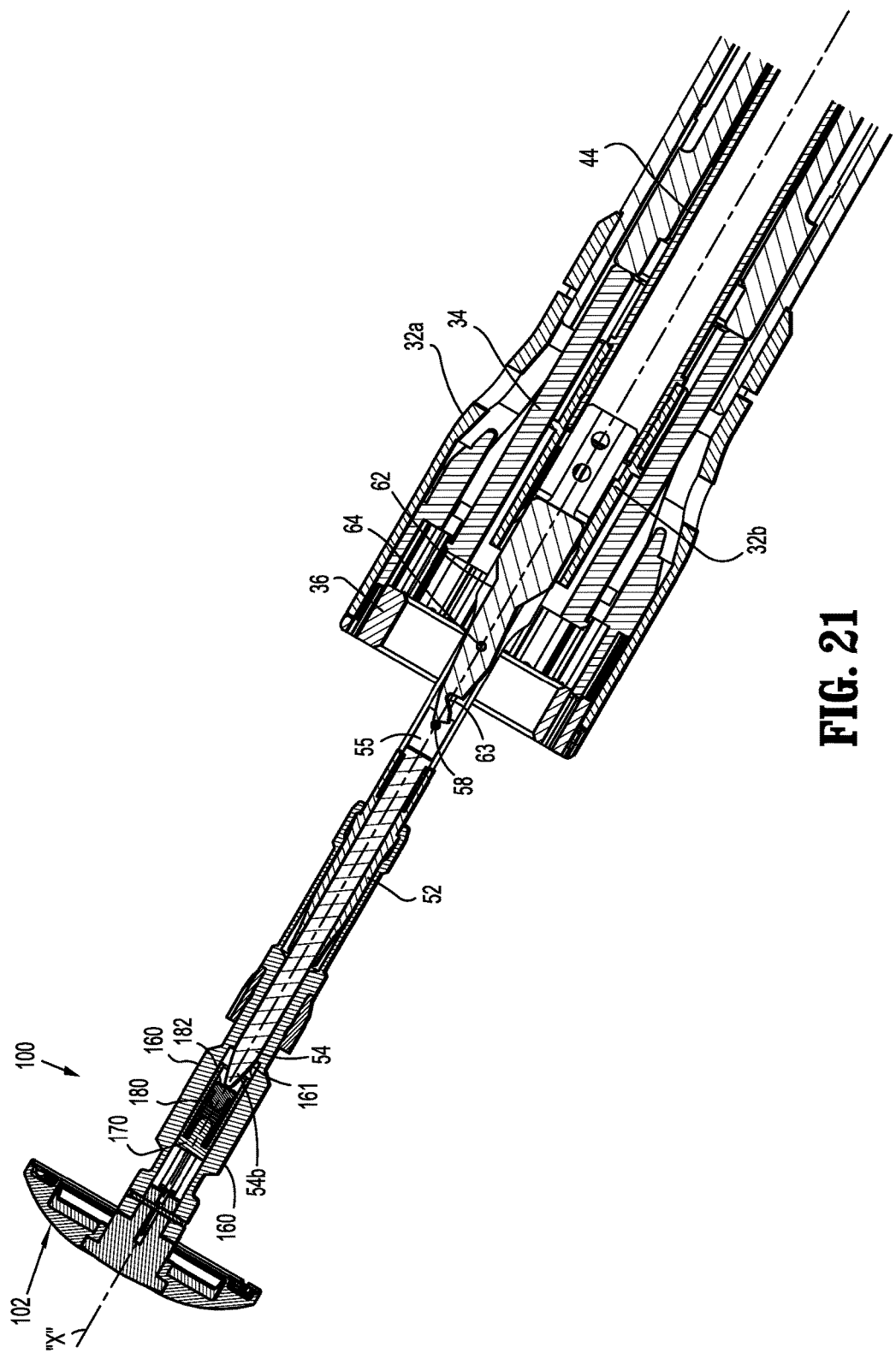
FIG. 21 is side cross-sectional view of the distal end of the central body portion and distal head portion of the surgical stapling device and the anvil assembly shown in FIG. 1 with the anvil assembly in its unapproximated position and the anvil head in the operative position.

Referring now to FIGS. 5-7, anvil assembly 100 is configured for releasable attachment to stapling device 10 (FIG. 1). Anvil assembly 100 includes a head assembly 102 and a rod assembly 104. Head assembly 102 is pivotally secured to rod assembly 104 and is configured to selectively move between a tilted position (FIG. 5) and an operative position (FIG. 21).

With particular reference to FIG. 7, head assembly 102 includes an anvil head 110, an anvil post 120, a cutting ring 130, a cover 140, and an anvil plate 150. Rod assembly 104 includes an anvil center rod 160, a first slide member 170, a second slide member 180, first and second link members 190, 192 pivotally connecting first and second slide members 170, 180 of rod assembly 104 with anvil post 120 of head assembly 102, and a spring member 196 for biasing first and second slide members 170, 180 relative to each other.

With reference still to FIGS. 5-7, anvil head 110 of head assembly 102 defines a centrally located throughbore 111 configured to receive anvil post 120, an inner annular recess 113 configured to receive cut ring 130, and an outer annular recess 115 configured to receive anvil plate 150. Inner annular recess 113 and outer annular recess 115 are separated by an annular flange 116 defines a notch 116a. Anvil head 102 further defines a first set of openings 117a configured to receive a first or retaining suture "$S_1$" and a second set of openings 117b configured to receive a second or guide suture "$S_2$". As will be described in further detail below, first suture "$S_1$" is a component of tubular guide assembly 202 of anvil delivery system 200 and second suture "$S_2$" is a component of suture guide assembly 204 of anvil delivery system 200.

Anvil post 120 is configured to be secured within throughbore 111 of anvil head 110. Anvil post 120 defines lateral slot 121 configured to accommodate first and second link members 190, 192, a large transverse bore 123 extending across longitudinal slot 121 for receiving a pivot member 106, and a pair of small transverse bores 115a, 115b extending across longitudinal slot 121 for receiving pivot pins 106a, 108a, respectively. Pivot member 106 pivotally connects anvil post 120 to a distal end 160b of center rod 160 via a cooperating bore 163 formed in center rod 160. In one embodiment, pivot member 106 includes a pin or post which defines a transverse axis which is spaced laterally from the longitudinal axis "x" defined by center rod 160 such that anvil head 110 can pivot approximately ninety degrees (90°) from an operative position (FIG. 21) in which a plane defined by tissue contacting surface 152 of anvil plate 150 of head assembly 102 is substantially perpendicular to the longitudinal axis "x" of center rod 160 to a tilted reduced profile position (FIG. 28) in which head assembly 110 is substantially parallel to longitudinal axis "x" of center rod 160. Alternately, other types of pivot members at a variety of locations in relation to longitudinal axis "x" of center rod 160 may be incorporated into anvil assembly 100. Pivot pins 106a, 108a pivotally connect first and second links 190, 192 of rod assembly 104 with anvil post 120.

Referring also to FIGS. 5 and 7, cutting ring 130 defines a throughbore 131 configured to be positioned about anvil post 112 and has a radial slot 133 configured to align with first set of openings 117a in anvil head 110. When cutting ring 130 is received within inner annular recess 113 of anvil head 110, radial slot 133 is configured to accommodate second suture "$S_2$" of suture guide assembly 204 of anvil delivery system 200 which is received through the second set of openings 117b. Cover 140 defines a throughbore 141 and is configured to be received between cutting ring 130 and anvil plate 150. Cover 140 may be formed of Mylar® or other protective material.

Anvil plate 150 includes a tissue contacting surface 152 defining a plurality staple forming recesses 153. Anvil plate 150 further includes a tab 154 configured to be received within a slot 115a formed in anvil head 110. Tab 154 and slot 115a cooperate to position anvil plate 150 in the proper orientation within outer recess 115 of anvil head 110.

Referring to FIGS. 5-7, center rod 160 of rod assembly 104 includes proximal and distal ends 160a, 160b and defines a throughbore 161. As shown, proximal end 160a includes at least one opening 165 configured to receive a suture or the like to facilitate positioning of anvil assembly 100 within a hollow organ. A distal end of throughbore 161 (see FIG. 18) is configured to slidably receive at least a portion of each of first and second slide members 170, 180.

With particular reference to FIG. 7, first slide member 170 of rod assembly 104 includes a substantially annular body having an open proximal end 170a and a closed distal end 170b and defining a throughbore 171 extending between proximal and distal ends 170a, 170b. Throughbore 171 is configured to accommodate spring member 196. First slide member 170 further defines a longitudinal cut-away 173 which extends between proximal and distal ends 170a, 170b and is in communication with throughbore 173. Cutaway 173 is configured to accommodate second slide member 180 such that first and second slide members 170, 180 may slide relative to each other. Distal end 170b of first slide member 170 includes a radially outward extending flange 172 defining a transverse bore 175 configured to receive pivot pin 106b. Pivot pin 106b secures a first end 190a of first link 190 of rod assembly 104 to the first slide member 170. A second end 190b of first link 190 is secured with anvil post 120 of head assembly 102 by a pivot pin 106a. Distal end 170b further includes a nub 174 extending proximally within throughbore 171 configured to support and align a distal end 196b of spring member 196 within throughbore 171.

Second slide member 180 of rod assembly 104 is configured for longitudinal movement relative to first slide member 170. Second slide member 180 includes a longitudinal body having a closed proximal end 180a, an open distal end 180b, and is configured to be received in the cut-away 173 of first slide member 170. As noted above, this configuration permits sliding of first slide member 170 in relation to second slide member 180. A radially outward extending flange 182 extends along a majority of the length of second slide member 180 and defines a transverse bore 185 configured to receive pivot pin 108b for securing second link 192 of rod assembly 104 with anvil post 120 of head assembly 102. A proximal end 180a of second slide member 180 includes a distally extending nub 184 which supports and aligns a proximal end 196a of spring member 196 within throughbore 171.

Figure 28:
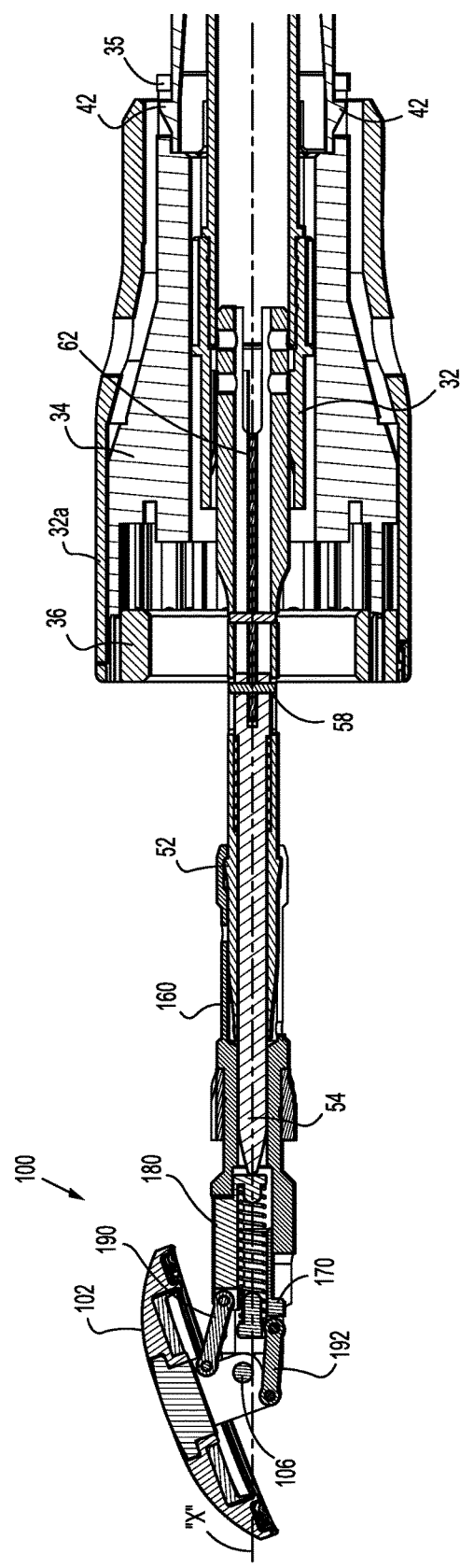
FIG. 28 is a cross-sectional view of the distal end of the central body portion and distal head portion shown in FIG. 27 after the anvil head has been unapproximated and pivoted to the tilted position.

A spring or biasing member, e.g., coil spring 196, is positioned between first and second slide members 170, 180 to urge the slide members apart or away from each other. First or drive link 190 is pivotally connected at a proximal end 190a to second slide member 180 by pivot pin 106a and is pivotally connected at a distal end 190b to anvil post 120 by pivot pin 106b. Second or return link 192 is pivotally connected at a proximal end 192a to first slide member 170 by pivot pin 108a and is pivotally connected at a distal end 192b to anvil post 120 by pivot pin 108b. First and second links 190, 192 are connected to slide members 170, 180 and anvil post 120 in such a manner that when biasing member 196 urges first and second slide members 170, 180 apart, anvil head 110 pivots about pivot member 106 to its tilted reduced profile position (FIG. 28).

Center rod 160 includes a plurality of flexible arms 164 which defines a proximal end of throughbore 161 and is configured to releasably engage a removable trocar, adaptor and/or the annular protrusion 60 of the body portion 52 of the anvil retainer assembly 50. A plurality of splines 166 are formed about center rod 160. Splines 166 mesh with grooves (not shown) formed in stapling device 10 (FIG. 1) to properly align anvil assembly 100 in relation to shell assembly 30 (FIG. 3) of stapling device 10 during approximation of anvil assembly 100 and shell assembly 30.

In any of the embodiments disclosed herein, the pivoting anvil assembly, which includes a head assembly and a rod assembly, may be arranged differently. For example, see the tilting anvil assembly disclosed in U.S. patent application Ser. No. 13/915,953, the disclosure of which is hereby incorporated by reference herein in its entirety.

Figure 9:
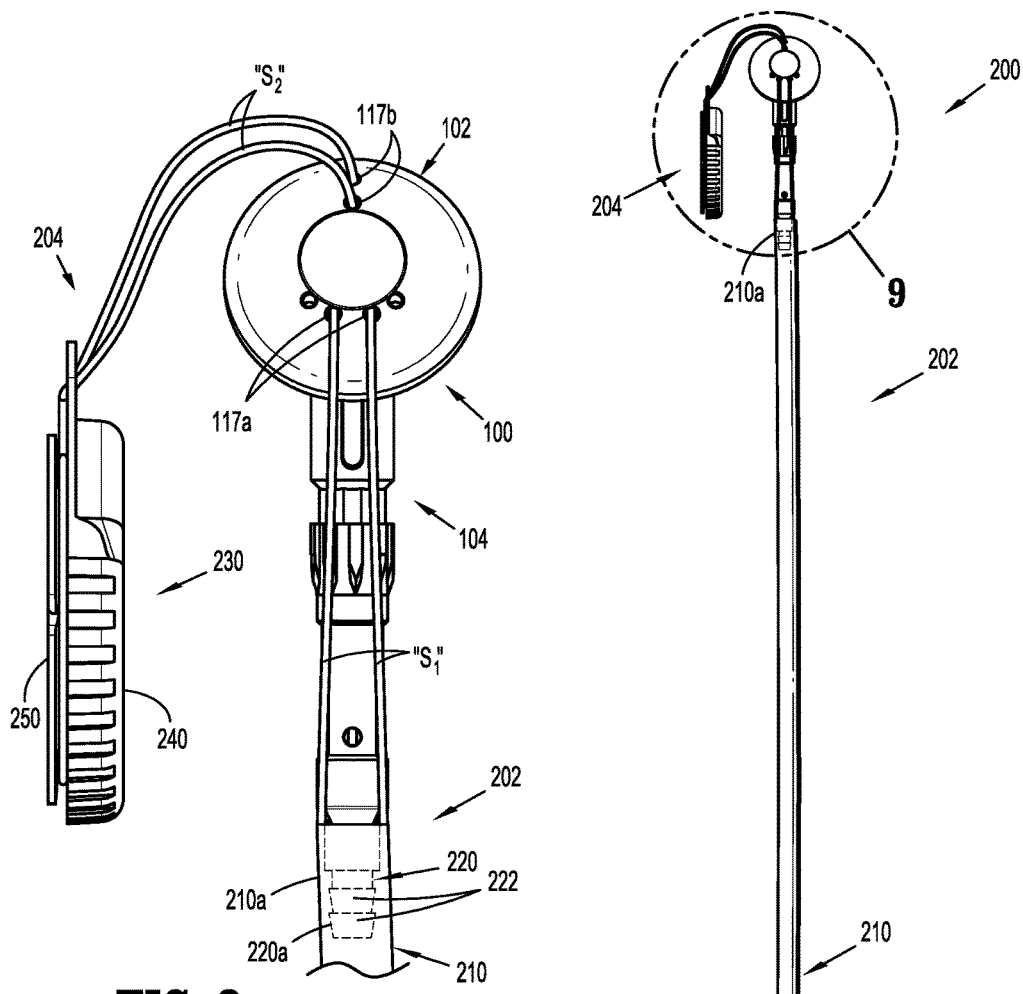
FIG. 9 is an enlarged view of the indicated area of detail shown in FIG. 8.
Figure 8:
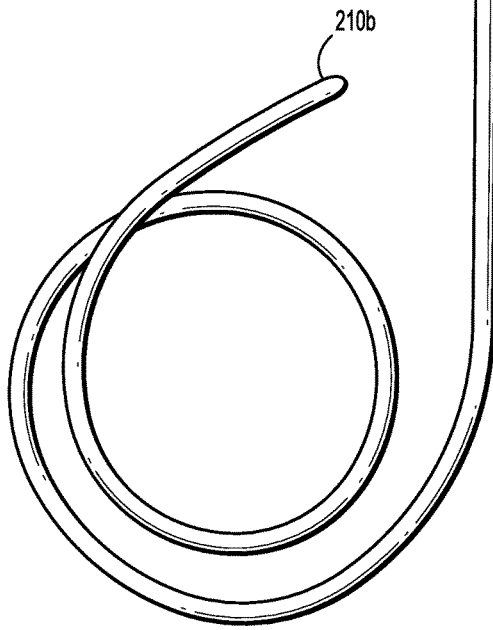
FIG. 8 is a side view of an anvil delivery system, including a tubular guide assembly and a suture guide assembly, attached to the anvil assembly shown in FIG. 5, with the anvil head positioned in the tilted reduced profile position.
Figure 10:
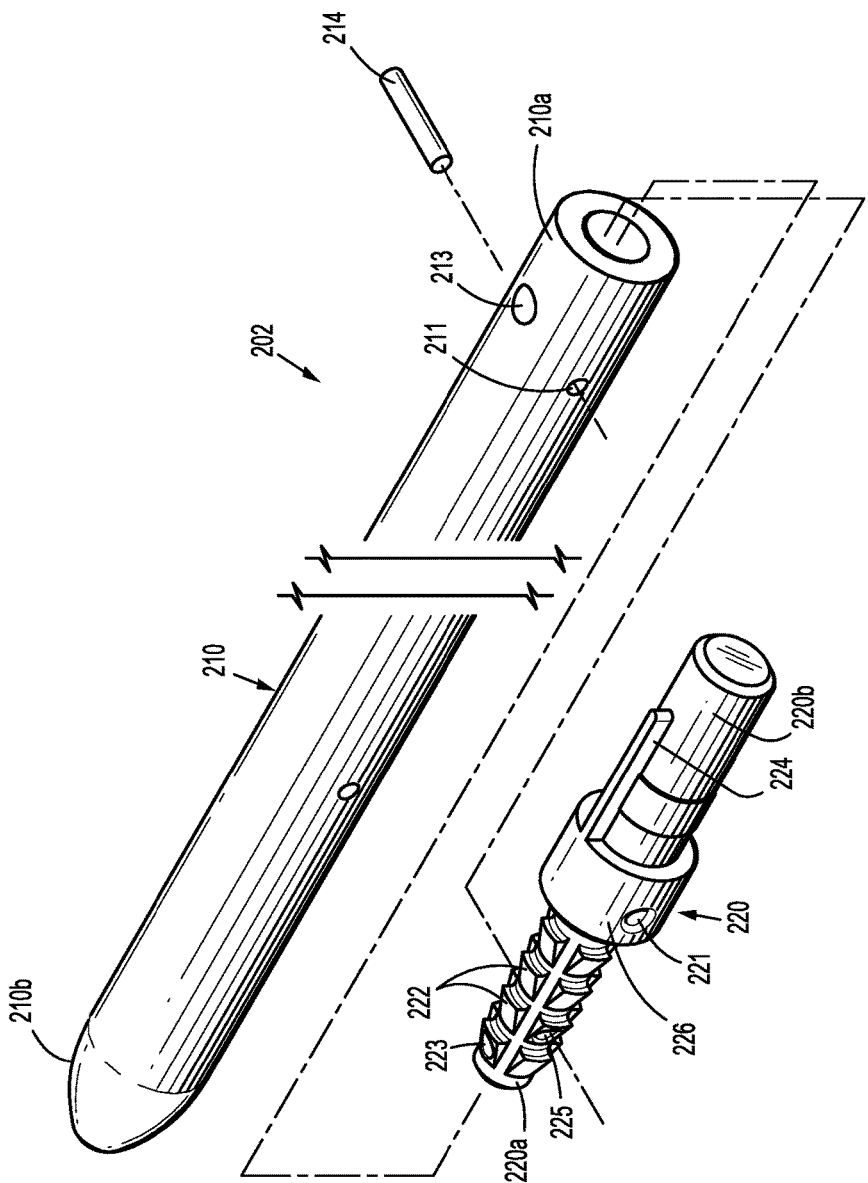
FIG. 10 is an enlarged perspective view of a tubular member and an adapter of the tubular guide assembly shown in FIG. 8.
Figure 11:
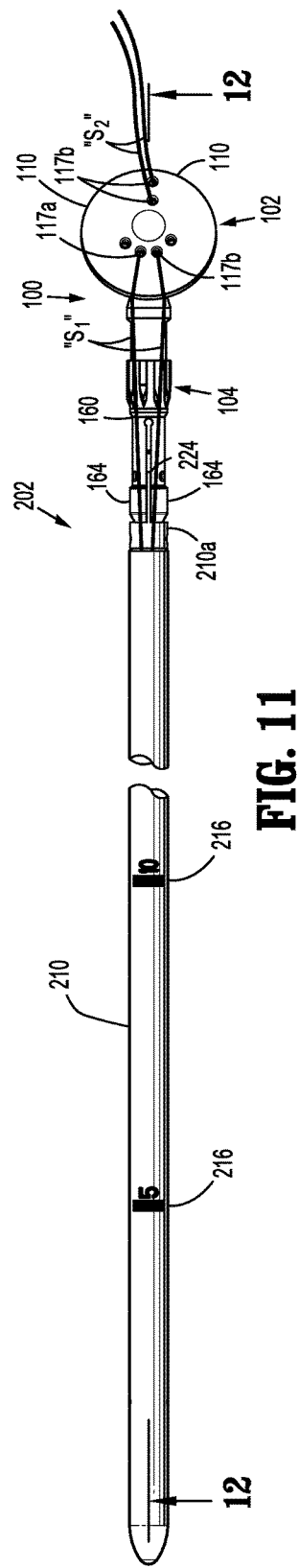
FIG. 11 is an side view of the anvil delivery system shown in FIG. 8, including the anvil assembly shown in FIGS. 5-7 shown in the first tilted position and a first suture.

With reference now to FIGS. 8 and 9, anvil assembly 100 is shown operably connected to a system for delivering anvil assembly 100 within a patient "P" (FIG. 25) shown generally as anvil delivery system 200. Anvil delivery system 200 includes a tubular guide assembly 202 and a suture guide assembly 204. Each of tubular and suture guide assemblies 202, 204 are selectively secured to anvil assembly 100 to facilitate trans-oral positioning of anvil assembly 100 within a patient. As will be described in further detail below, tubular guide assembly 202 is configured to be manually detached from anvil assembly 100 prior to attachment of anvil assembly 100 to stapling device 10 (FIG. 1) and suture guide assembly 204 is configured to be automatically detached from anvil assembly 100 following the stapling stroke of the stapling device 10 (FIG. 1).

With reference now to FIGS. 8-12, tubular guide assembly 202 includes a flexible tube 210 for trans-oral positioning of anvil assembly 100 within a patient "P" (FIG. 20) and an adapter 220 for connecting flexible tube 210 to anvil assembly 100. Flexible tube 210 includes an open end 210a for supporting adapter 220 and a closed end 210b configured for trans-oral receipt in a patient. Open end 210a of flexible tube 210 defines a throughbore 211 configured to receive a locking pin 214. Open end 210a further includes an opening 213. Flexible tube 210 may include markings or other gradations 216 (FIG. 11) along the length thereof to indicate to a surgeon the depth of insertion of the flexible tube 210 within the patient during tran-oral positioning of anvil assembly 100 within a patient and/or to indicate the length of flexible tube 210 remaining in the patient during removal.

Adapter 220 includes a first end 220a configured to be received within open end 210a of flexible tube 210 and a second end 220b configured to be received within bore 161 formed in center rod 160 of anvil assembly 100. A first end 220a of adapter 220 includes a series of annular rings 222 configured to frictionally retain first end 220a of adapter 220 within open end 210a of flexible tube 210. A second end 220b of adapter 220 includes a longitudinal guide member 224 configured to be received between two adjacent flexible arms 164 of center rod 160 of anvil assembly 100. Second end 220b of adapter 220 is sized to allow center rod 160 of anvil assembly 100 to freely slide onto and off of second end 220b of adapter 220. Adapter 220 further defines a first throughbore 221 formed in a central hub portion 226 as well as second and third throughbores 223, 224 formed in first end 220a. Throughbore 223 is configured to align with throughbore 211 formed in open end 210a of flexible tube 210 and is sized to receive locking pin 214. Throughbore 223 is configured to receive both ends of the first suture "S₁." Throughbore 221 can also receive the suture ends to enhance retention. For a more detailed description of an exemplary tubular guide assembly including a flexible tube and an adapter, please refer to commonly owned U.S. Pat. No. 8,109,426, the content of which is incorporated by reference herein in its entirety.

Figure 12:
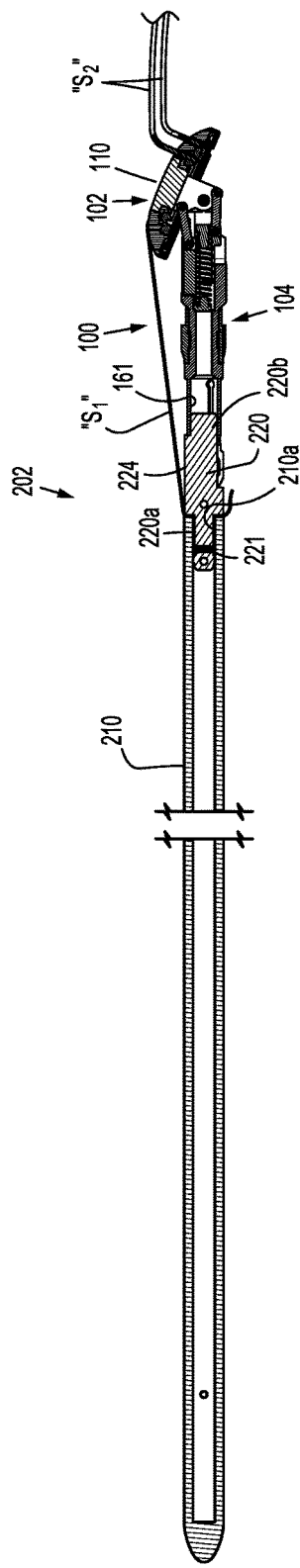
FIG. 12 is a side cross-sectional view taken along section line 12-12 of FIG. 11.

In order to secure anvil assembly 100 on tubular guide assembly 202 of anvil delivery system 200, first suture "S₁" is threaded through openings 117a formed on anvil head 110 such that first and second ends of first suture "S₁" are positioned on different sides of center rod 160. Second end 220b of adapter 220 is positioned within throughbore 161 of center rod 160 such that longitudinal guide 224 (FIG. 10) of adapter 220 is received between two arm members 164 (FIG. 7) of center rod 160. Each of the first and second ends of first suture "S₁" is then inserted through throughbore 223 formed in adapter 220. Anvil head 110 is then rotated to a first tilted position against the bias of spring 196 and the first and second ends of first suture "S₁" are pulled through opening 223 to apply tension on anvil head 110 to retain anvil head 110 in the first tilted position as shown in FIG. 12.

After first suture "S₁" is tensioned to retain anvil head 110 in the first tilted position, first end 220a of adapter 220 is inserted into open end 210a of flexible member 210. The frictional contact between annular rings 222 of first end 220a of adapter 220 and an inner surface of flexible tube 210 secures adapter 220 to flexible tube 210 and prevents first suture "S₁" from loosening as it is clinched between the outer wall of the adapter 220 and inner wall of flexible tube 210. It is envisioned that more than one suture may be used to secure anvil head assembly 110 in a pre-fired tilted position. It is also envisioned that first suture "S₁" need not be passed through bore 221 but instead can clamped between adapter 220 and the inner wall of the flexible tube 210.

Turning back to FIG. 9, suture guide assembly 204 of anvil delivery system 200 includes a reel assembly 230. Reel assembly 230 is configured to house and facilitate manipulation of second suture "S₂". Reel assembly 230 includes a housing 240 and a reel member 250.

Figure 14:
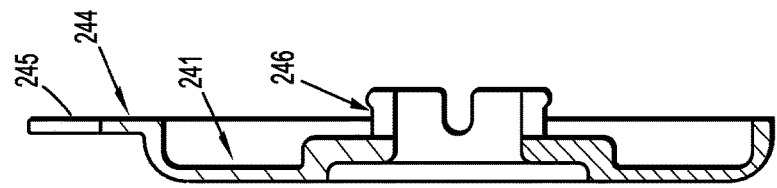
FIG. 14 is a side cross-sectional view of the housing shown in FIG. 14.
Figure 13:
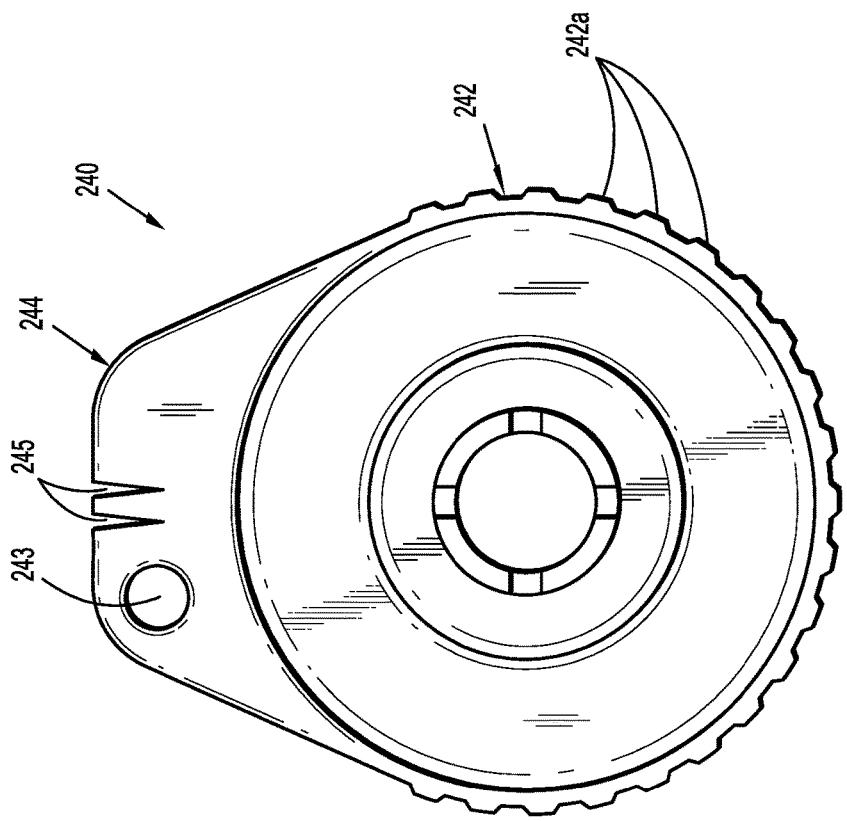
FIG. 13 is a top view of a housing of the suture reel of the suture guide assembly shown in FIG. 8.
Figure 15:
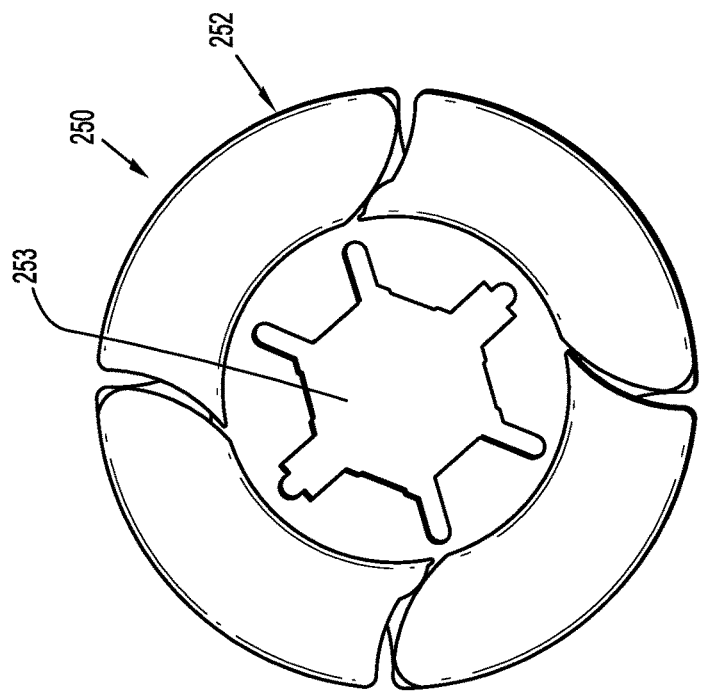
FIG. 15 is a top view of a reel member of the reel assembly of the suture guide assembly shown in FIG. 8.

With reference now to FIGS. 13 and 14, housing 240 of reel assembly 230 includes a substantially circular body 242 defining an annular cavity or recess 241. Circular body 242 may include a textured surface to facilitate operable engagement by a user, e.g. ribs 242a (FIG. 13). Housing 240 further includes a radially outward extending tab 244 and an annular flange 246. Tab 244 defines an opening 243 and a pair of slots 245. Opening 243 is configured to receive second suture "S₂" and operates to guide second suture "S₂" from reel member 250 (FIG. 15). Slots 245 are configured to selectively receive and secure second suture "S₂" once a sufficient length of second suture "S₂" is released from reel member 250.

Figure 16:
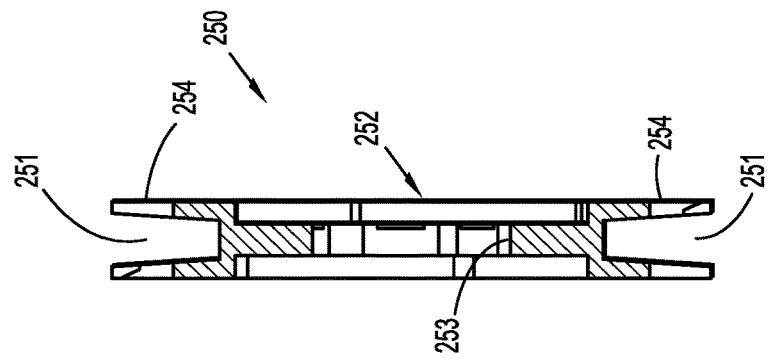
FIG. 16 is a side cross-sectional view of the reel member shown in FIG. 15.

Turning to FIGS. 15 and 16, reel member 250 of reel assembly 230 includes a substantially circular body 252 defining an annular recesses 251 extending about an outer perimeter 254 of circular body 252. Annular recess 253 is configured to receive second suture "S₂". Circular body 252 further defines an opening 253 configured to operably receive annular flange 246 of housing 240 such that circular body 252 is rotatably supported within annular cavity 241 of a housing 240. Circular body 252 is rotatably supported within housing 240 to permit the release of second suture "S₂" from within annular recess 251 of reel member 250.

Figure 17:
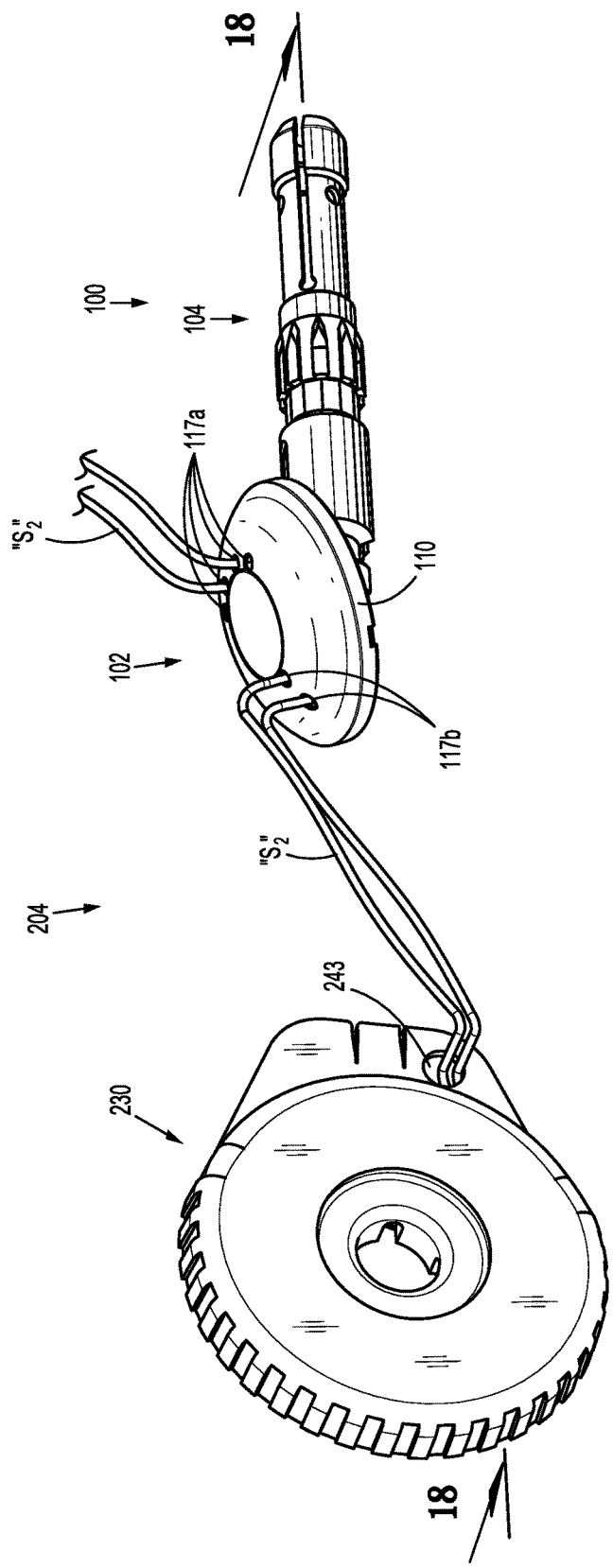
FIG. 17 is a perspective view of the suture guide assembly of the anvil delivery system shown in FIG. 8 attached to the anvil assembly shown in FIG. 5.

Referring to FIGS. 17-19, suture guide assembly 204 of anvil delivery system 200 is shown operably attached to anvil assembly 100. Although suture guide assembly 204 may be provided to a clinician pre-attached to anvil assembly 100, is envisioned that suture guide assembly 204 and anvil assembly 100 may be provided as separate components that can be attached to one another by a clinician prior to use. Second suture "S₂" is attached to anvil assembly 100 by threading an end of second suture "S₂" into a first opening of second openings 117b of anvil head 110, through slot 133 of cutting ring 130 and notch 116a of anvil head 110, and out a second opening of second openings 117b. First and second ends of second suture "S₂" are then threaded through opening 243 formed in tab 244 of housing 240 of reel assembly 230 and secured about reel member 250 of reel assembly 230. To secure second suture "S₂" to reel member 250, second suture "S₂" is wound in annular recess 251 about reel member 250. Reel member 250 is then secured to housing 240 by positioning reel member 250 within annular cavity 241 of housing 240 and positioning flange 246 of housing 240 within opening 253 of reel member 250.

Figure 20:
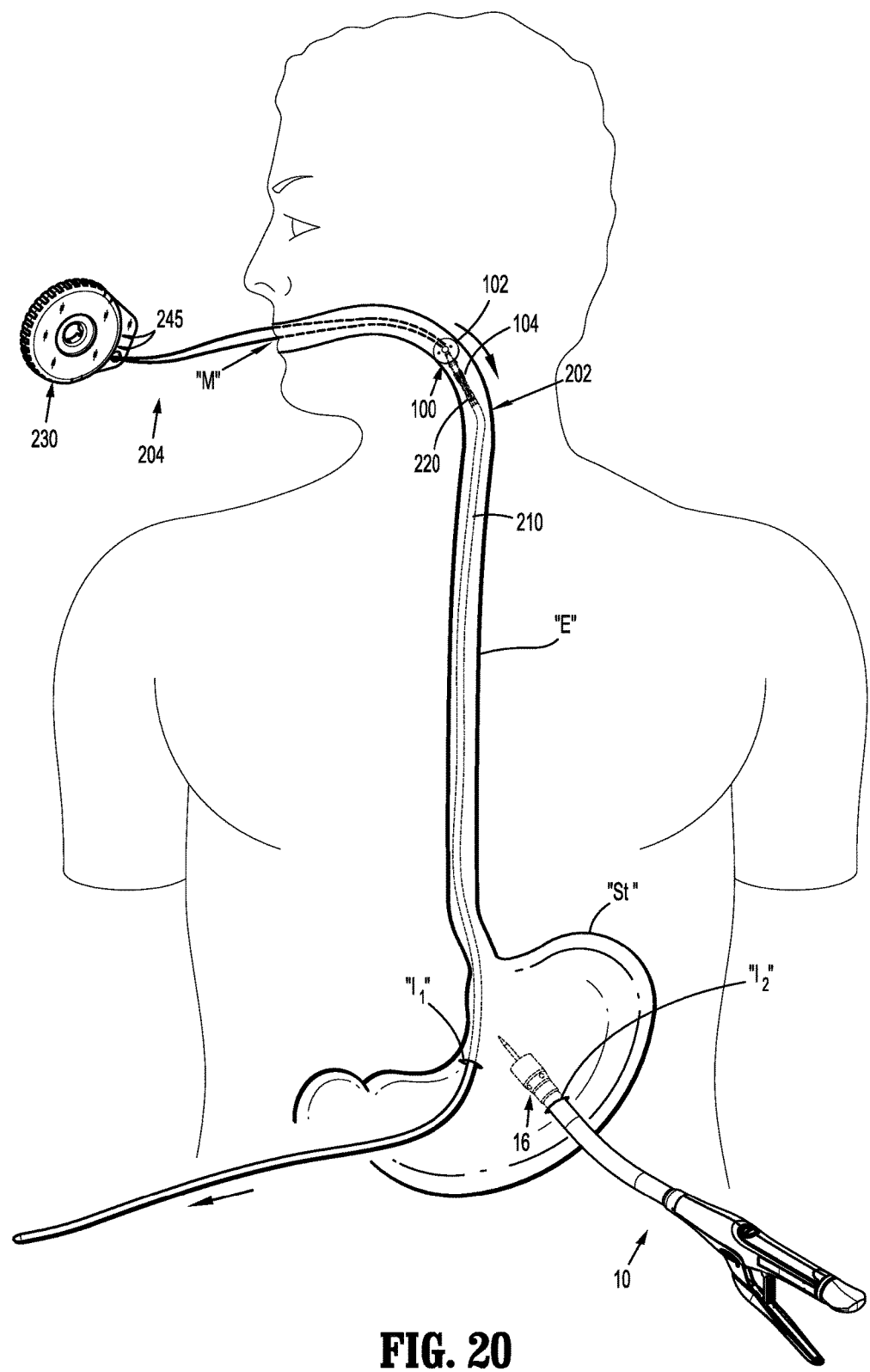
FIG. 20 is an illustration of the surgical stapling device shown in FIGS. 1 and 2 inserted into a stomach of a patient and the anvil delivery system with the connected anvil assembly shown in FIG. 8 being inserted trans-orally into a patient.

With reference now to FIG. 20, a method for delivering anvil assembly 100 to a surgical site within a patient will be described. In one method, anvil assembly 100 is provided in the first tilted position supported on tubular guide member 202 of anvil delivery system 200 and suture guide assembly 204 is attached to anvil head 110 such that anvil assembly 100 is ready for delivery. Alternatively, the suture guide assembly 204 and tubular guide assembly 202 can be provided separately from anvil assembly 100 and a clinician can secure anvil assembly 100 to tubular guide assembly 202 and/or suture guide assembly 204 of anvil delivery system 200 as discussed above. In this manner, tubular guide assembly 202, suture guide assembly 204, and/or anvil assembly 100 may be provided to a clinician as separate components, or together as kit. Once flexible tube 210 of tubular guide assembly 202 has been secured to anvil assembly 100 and second suture "S₂" of suture guide assembly 204 has been attached to anvil assembly 100, the surgeon inserts closed end 210b of flexible tube 210 in the patient's mouth "M" and moves closed end 210b along with flexible tube 210 down through esophagus "E" to a surgical site, e.g., the stomach "St". As anvil assembly 100 travels through esophagus "E" to the surgical site, second suture "S₂" is unwound from reel assembly 230 of suture guide assembly 204. Suture guide assembly 204 may be used at any point during insertion and prior to completion of the stapling procedure to retract anvil assembly 100 back through esophagus "E" and out of the patients mouth "M". Suture guide assembly 204 may also be used to manipulate anvil assembly 100 in the event anvil assembly 100 becomes stuck and/or, is not properly positioned within the patient "P".

After insertion, the surgeon then makes a first incision "I₁" at the surgical site (stomach "St" as shown) to provide access to closed end 210b of flexible tube 210. Thereafter, the surgeon pulls open end 52b of flexible tube 52 through first incision "I₁" to position the anvil assembly 100 at the surgical site. In some procedures it may be beneficial to pull flexible tube 210 through incision "I₁" until center rod assembly 104 of anvil assembly 100 advances through first incision "I₁". When anvil assembly 100 is properly positioned at the surgical site, the surgeon releases tubular guide assembly 202 of anvil delivery system 200 from anvil assembly 100 by cutting suture "S₁" and separating anvil assembly 100 from second end 20b of adapter 220. Flexible tube 210 and adapter 220 may then be pulled from the body through first incision "I₁". Second suture "S₂" of suture guide assembly 204 may also be secured within slots 245 formed in tab 244 of housing 240 of reel assembly 230.

In one method, a second incision "I₂" is then formed at the surgical site such that distal head portion 16 of stapling device 10 may be received therethrough. Alternatively, distal head portion 16 of stapling device 10 may be received through first incision "I₁" once tubular guide assembly 202 of anvil deliver system 200 has been removed therefrom.

Figure 22:
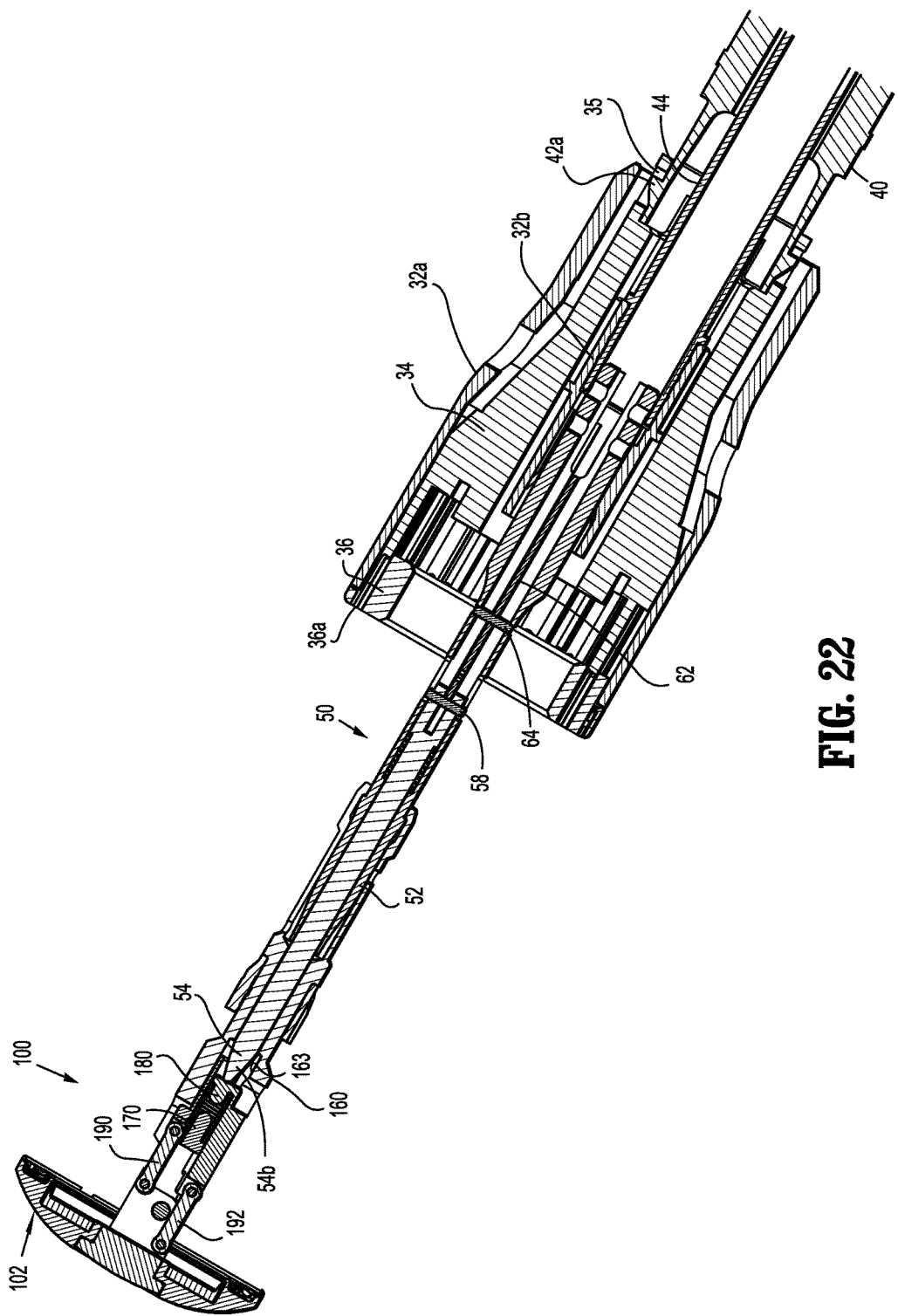
FIG. 22 is a cross-sectional view of the distal end of the central body portion and distal head portion shown in FIG. 21 ninety-degrees offset from the cross-sectional view of FIG. 21.

Referring to FIGS. 21 and 22, after stapling device 10 and anvil assembly 100 are positioned at the surgical site, anvil assembly 100 can be secured to stapling device 10 by inserting retractable trocar 54 into bore 161 of center rod 160 of anvil assembly 100. Because the anvil retainer assembly 50 is unapproximated when anvil assembly 100 is attached and stapling device 10 (FIG. 1) has yet to be fired, trocar 54 is in its advanced position. When trocar 54, in its advanced position, is inserted into center rod throughbore 161, tip 54b of trocar 52 engages base portion 182 of second slide member 180 and moves second slide member 180 towards first slide member 170 to move anvil head 110 from its tilted position to its operative, non-tilted position via links 190, 192 with anvil head 110 in its operative position, tissue to anastomosed can be secured about anvil center rod 160 using known techniques.

Figure 23:
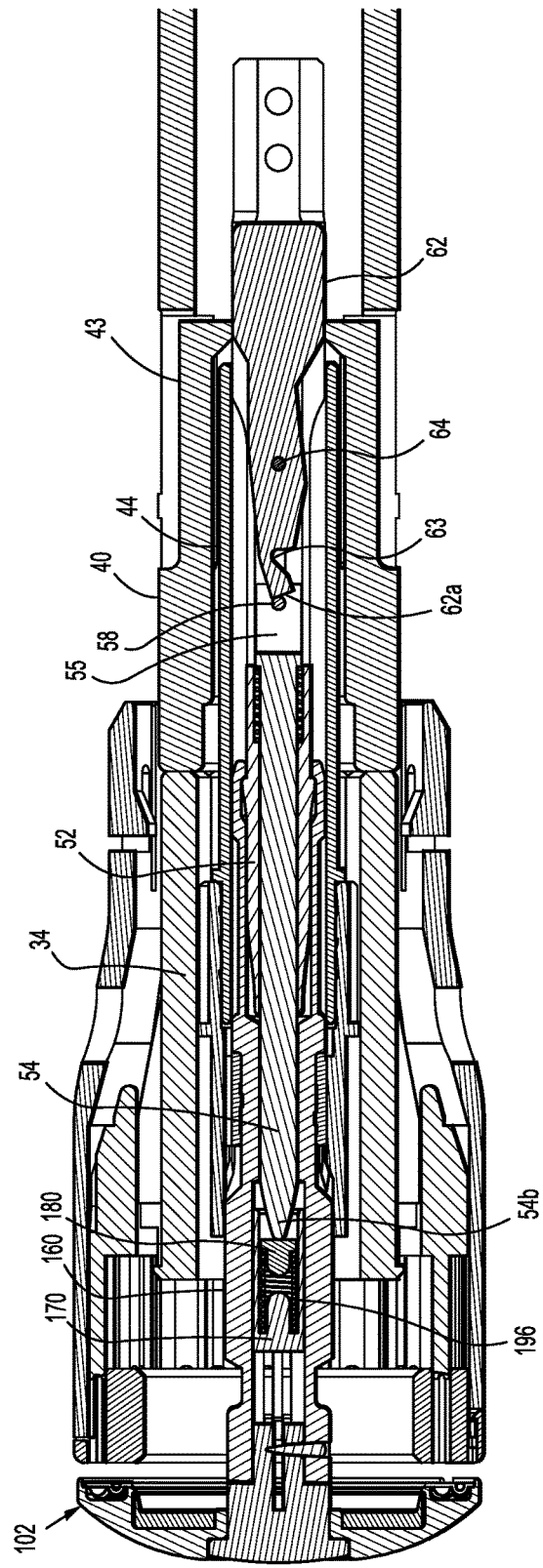
FIG. 23 is a cross-sectional view of the distal end of the central body portion and distal head portion shown in FIG. 21 with the anvil head in the approximated position.
Figure 24:
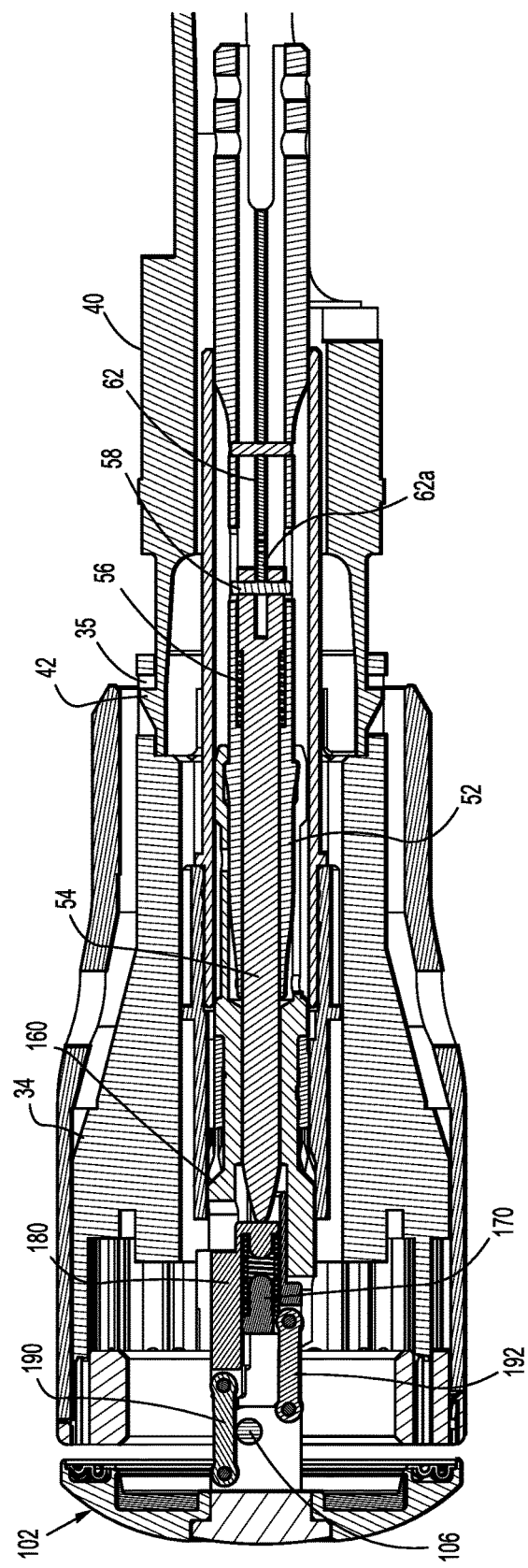
FIG. 24 is a cross-sectional view of the distal end of the central body portion and distal head portion shown in FIG. 22 ninety-degrees offset from the cross-sectional view of FIG. 23 with the anvil head in the approximated position.

Referring to FIGS. 23 and 24, when the anvil assembly 100 and shell assembly 30 are approximated, cam member 62 is prevented from pivoting by bushing 44 and arms 43 of pusher 40. Since cam member 62 is not free to pivot, finger 62a is positioned to prevent pin 58 from moving proximally within body portion 52 of anvil retainer assembly 50 to prevent retraction of trocar 54. As such, trocar tip 54b engages second slide member 180 to retain second slide member 180 in its advanced position. As such, anvil head 102 is retained in the operative, non-tilted position.

Figure 25:
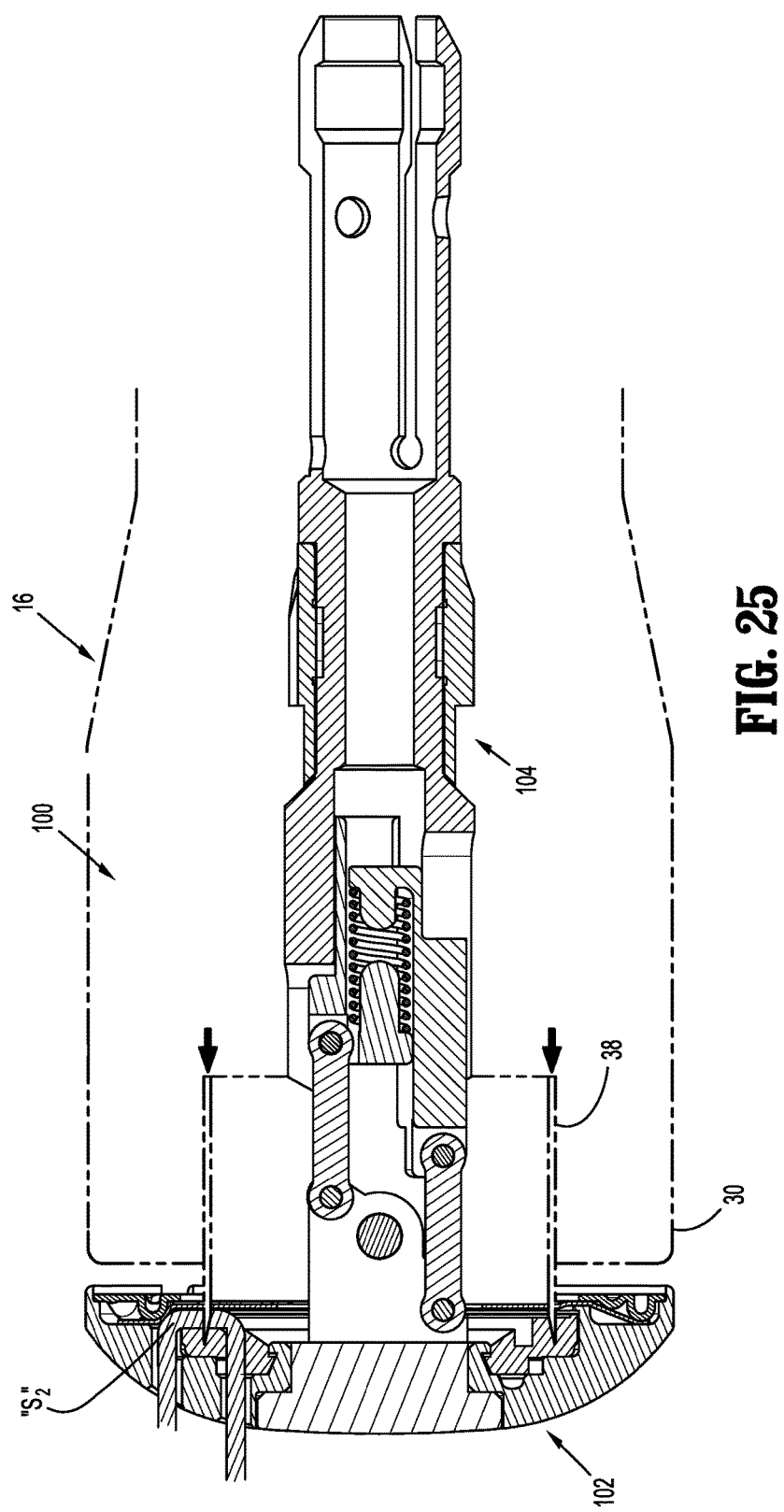
FIG. 25 is a cross-sectional side view of the anvil assembly shown in FIG. 24 with the distal end portion of the surgical stapling device including a knife blade shown in phantom during firing of the stapling device.

With reference now to FIG. 25, stapling device 10 (FIG. 1) may then be fired. During firing of stapling device 10, knife blade 38 mounted within shell assembly 30 on distal end portion 16 of stapling device 10 is advanced distally into engagement with head assembly 102 of anvil assembly 100. In some embodiments, knife blade 38 can be advanced subsequent to and/or independently of pusher 40. Distal advancement of knife blade 38 causes knife blade 38 to pass through cover 140 and into cutting ring 130 of anvil assembly 100. As knife blade 38 engages cutting ring 130, second suture "S₂" which is received within slot 133 of cutting ring 130 is severed. As such, second suture "S₂" and suture guide assembly 204 is disconnected from anvil assembly 100. As noted above, prior to firing of stapling device 10 (FIG. 1), suture guide assembly 204 may be used to facilitate position of anvil assembly 100 and/or to retract anvil assembly 100 back through the patient's mouth "M" (FIG. 20). By severing second suture "S₂", second suture "S₂" does not need to be retracted through second openings 117b (FIG. 19) to detach second suture "S₂" from anvil assembly 100. This reduces the likelihood of any tissue damage caused by friction while retracting second suture "S₂" from head assembly 102. Further, by not having to retract second suture "S₂" through second openings 117b in head assembly 102 of anvil assembly 100, the likelihood of introducing bacteria or other foreign material into the patient is reduced.

Figure 26:
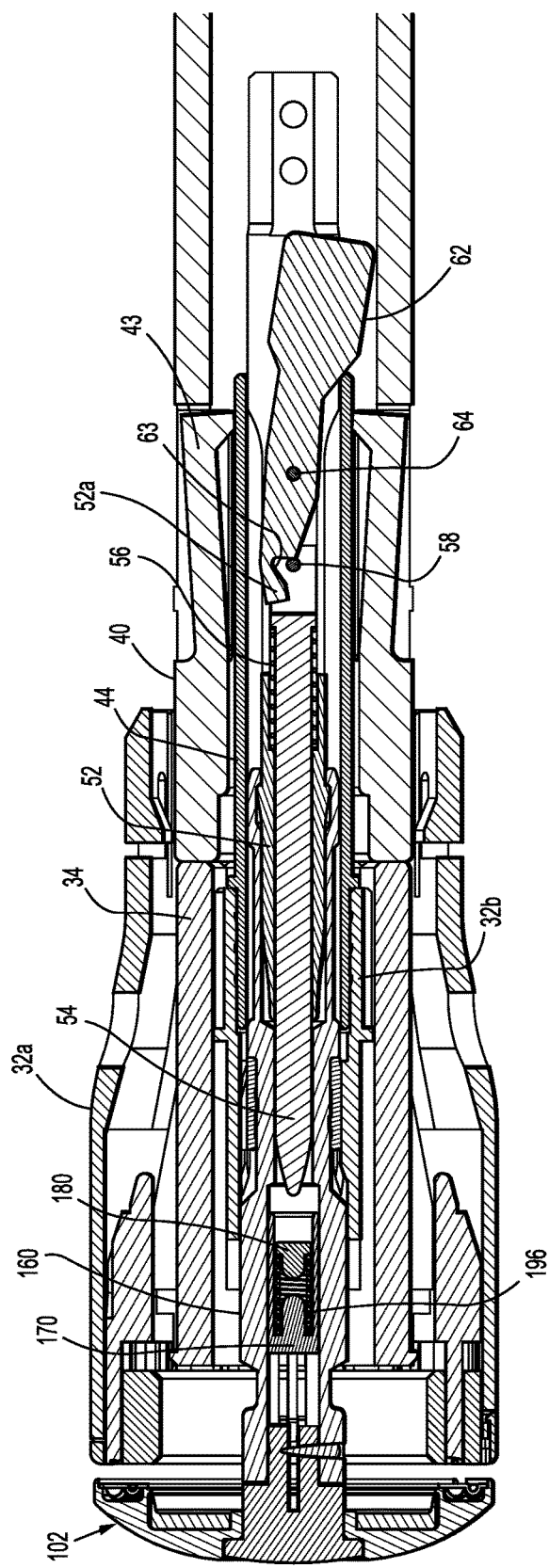
FIG. 26 is a cross-sectional view of the distal end of the central body portion and distal head portion shown in FIG. 23 with the anvil head in the approximated position after the stapling device has been fired.
Figure 27:
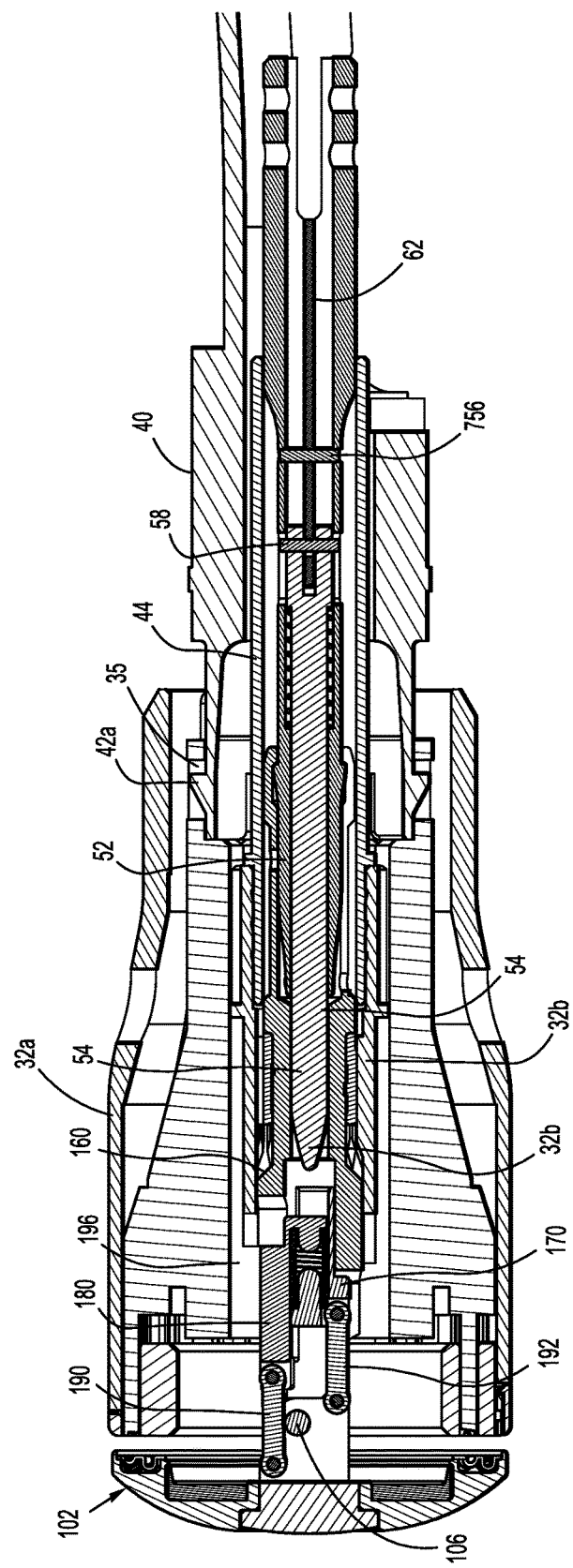
FIG. 27 is a cross-sectional view of the distal end of the central body portion and distal head portion shown in FIG. 24 offset ninety degrees from the cross-sectional view of FIG. 26 after the stapling device has been fired.

Referring to FIGS. 26 and 27, when stapling device 10 (FIG. 1) is fired and pusher 40 is moved distally about bushing 44, arms 43 of pusher 40 are deformed outwardly away from cam member 62. Engagement between pin 58 and the angled face of finger 62a causes cam member 62 to pivot. When cam member 62 pivots, pin 58 moves proximally into recess 63 of cam member 62 and trocar 54 moves to its retracted position within longitudinal bore 53 of body portion 52 under the bias of spring 56. As trocar 54 moves to its retracted position, biasing member 196 urges first and second slide members 170, 180 apart to urge anvil head 110 to its tilted reduced profile position (see FIG. 28). Because of the proximity of anvil head 110 to shell assembly 30, anvil head 110 will only move to its tilted reduced profile position during unapproximation of anvil assembly 100 and shell assembly 30. Anvil assembly 100 may then be removed from the surgical site and the surgical procedure may be completed in a traditional manner.

In further embodiments, the suture can be attached to the anvil assembly at a location that is not near the knife or cut ring. In this way, the knife does not sever the suture. The procedure is carried out as discussed above, except that one leg only of the suture is cut and then the suture guide assembly and suture are removed. Then, the anvil assembly is attached to the instrument, attachment actuating the movement of the anvil away from the tilted position, and the instrument is fired. Firing initiates movement of the anvil from the operative position back to the tilted position.

It will be understood that various modifications may be made to the embodiments disclosed herein. For example, the slotted cutting ring may be incorporated into anvil assemblies having alternative configurations. Therefore, the above description should not be construed as limiting, but merely as exemplifications of preferred embodiments. Those skilled in the art will envision other modifications within the scope and spirit of the claims appended hereto.

What is claimed is:

1. An anvil assembly comprising:
    an anvil center rod;
    a head assembly pivotally secured to the anvil center rod about a pivot axis and movable between an operative position and a tilted position, the head assembly including an anvil head and a cutting ring disposed within the anvil head, the anvil head defining first and second openings and the cutting ring defining a slot in alignment with the first and second openings;
    a suture disposed in the first and second openings; and
    a suture guide assembly including a reel member.

2. The anvil assembly of claim 1, wherein the first and second openings and the slot are dimensioned to receive the suture.

3. The anvil assembly of claim 1, wherein the anvil center rod includes first and second slide members, the first slide member being pivotally connected to the head assembly on one side of the pivot axis by a first drive link and the second slide member being connected to the head assembly on the other side of the pivot axis by a second drive link, the first slide member being movable in relation to the second slide member to effect movement of the head assembly between the operative position and the tilted position.

4. The anvil assembly of claim 1, further comprising an anvil tilting mechanism.

5. The anvil assembly of claim 3, further including a biasing member positioned to urge the first slide member in relation to the second slide member to position the head assembly in the tilted position.

6. The anvil assembly of claim 5, wherein the biasing member is positioned between the first member and the second slide member to urge the first and second slide members apart.

7. The anvil delivery system of claim 1, wherein the guide suture is received through the first opening in the anvil head, passes through the slot in the cutting ring, and extends from the second opening in the anvil head.

8. The anvil delivery system of claim 1, wherein the reel assembly includes a housing and a reel member rotatably received within the housing, wherein the guide suture is supported about the reel member.

9. The anvil delivery system of claim 8, wherein the reel member defines an annular channel for receiving the guide suture.

10. The anvil delivery system of claim 8, wherein the reel member is rotatably supported on the housing within an annular cavity in the housing.

11. The anvil delivery system of claim 1, further including a tubular guide assembly for trans-oral insertion of the anvil assembly.

12. The anvil delivery system of claim 11, wherein the tubular guide assembly includes a flexible tube and an adapter configured for operably connecting the flexible tube to the anvil center rod.

13. The anvil delivery system of claim 12, wherein the tubular guide assembly further includes a retaining suture for retaining the head assembly of the anvil assembly in the tilted position.

14. The anvil delivery system of claim 13, wherein the retaining suture is received through third and fourth openings in the anvil head and is secured between the adapter and the flexible tube.

15. A kit comprising:
   an anvil assembly according to claim 1;
   a suture guide assembly including a guide suture and a reel assembly; and
   a tubular guide assembly including a flexible tube and an adapter.

\* \* \* \* \*